United States Patent [19]
Lewicki et al.

[11] Patent Number: 4,804,650
[45] Date of Patent: Feb. 14, 1989

[54] ANALOGS OF ATRIAL NATRIURETIC PEPTIDES

[75] Inventors: John A. Lewicki, San Jose; Robert M. Scarborough, Jr., Hayward; Lorin K. Johnson, Pleasanton, all of Calif.

[73] Assignee: Biotechnology Research Associates, J.V., Mountain View, Calif.

[21] Appl. No.: 168,661

[22] Filed: Mar. 16, 1988

Related U.S. Application Data

[63] Continuation of Ser. No. 921,360, Oct. 28, 1986, abandoned.

[51] Int. Cl.⁴ .................. A61K 37/02; C07K 7/06
[52] U.S. Cl. ............................ 514/15; 514/16; 514/17; 530/327; 530/328; 530/329; 530/330
[58] Field of Search ................ 514/16, 15, 17; 530/327, 328, 329, 330

[56] References Cited

U.S. PATENT DOCUMENTS

| 4,496,544 | 1/1985 | Needleman | 514/13 |
| 4,508,712 | 4/1985 | Needleman | 514/11 |
| 4,557,864 | 12/1985 | Needleman | 530/326 |
| 4,607,023 | 8/1986 | Thibault et al. | 574/11.5 |
| 4,609,725 | 9/1986 | Brady et al. | 530/324 |
| 4,618,600 | 10/1986 | Johnson et al. | 530/325 |
| 4,643,989 | 2/1987 | Baird | 514/12 |
| 4,647,455 | 3/1987 | DuBold | 424/95 |
| 4,652,549 | 3/1987 | Blaine | 514/12 |
| 4,656,158 | 4/1987 | Matsuo et al. | 530/324 |
| 4,657,891 | 4/1987 | Matsuo et al. | 530/304 |
| 4,663,437 | 5/1987 | deBold | 530/324 |
| 4,670,540 | 6/1987 | Sakakibara | 530/324 |
| 4,673,732 | 6/1987 | Kiso et al. | 530/326 |

Primary Examiner—Delbert R. Phillips
Attorney, Agent, or Firm—Ciotti & Murashige, Irell & Manella

[57] ABSTRACT

Compounds and compositions comprising synthetic analogs of Atrial Natriuretic Peptides are provided, together with methods for their production and use as natriuretics, diuretics and/or vasodilators, or as intermediates for or modulators of such useful compounds or of native Atrial Natriuretic Peptides.

5 Claims, 9 Drawing Sheets

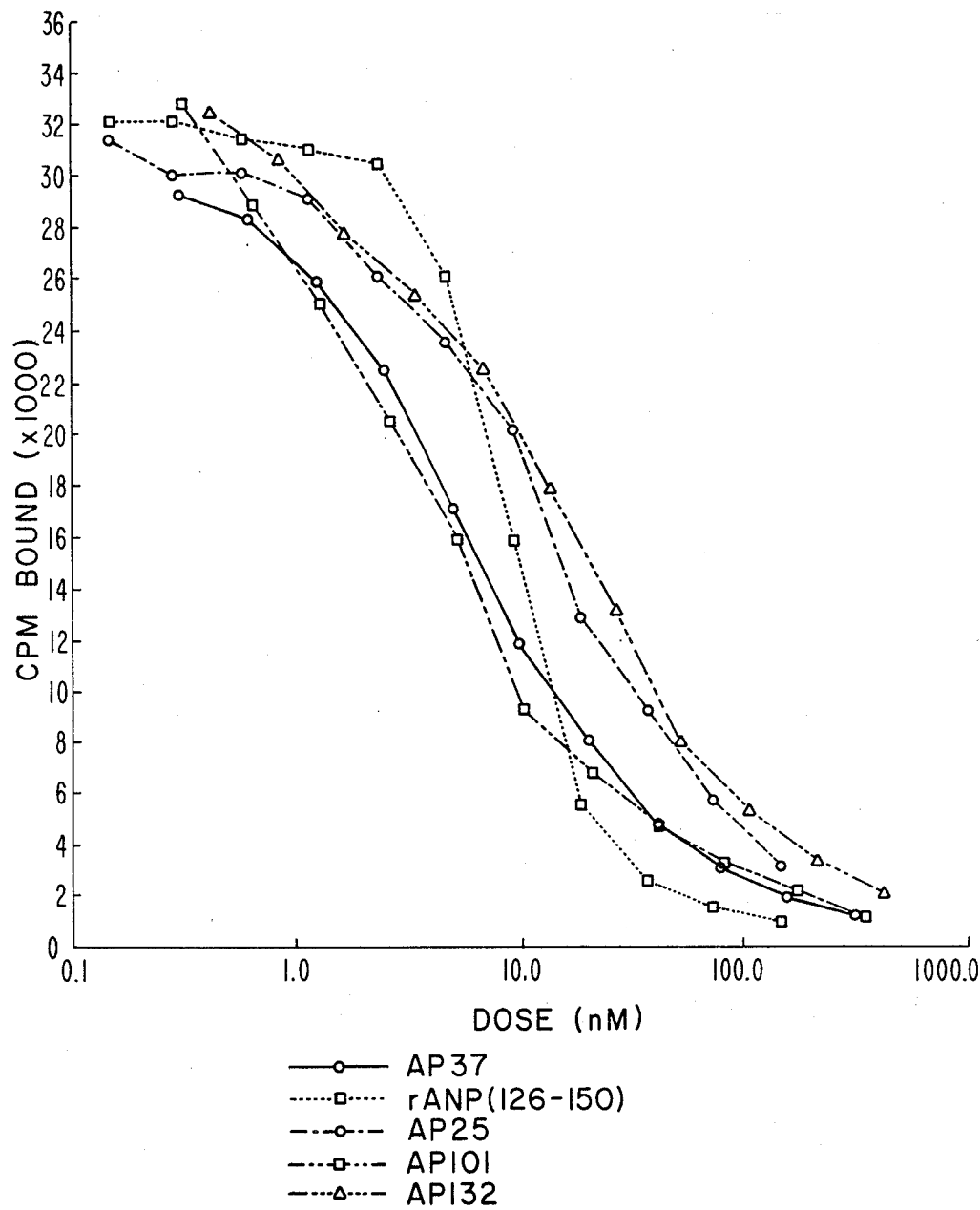

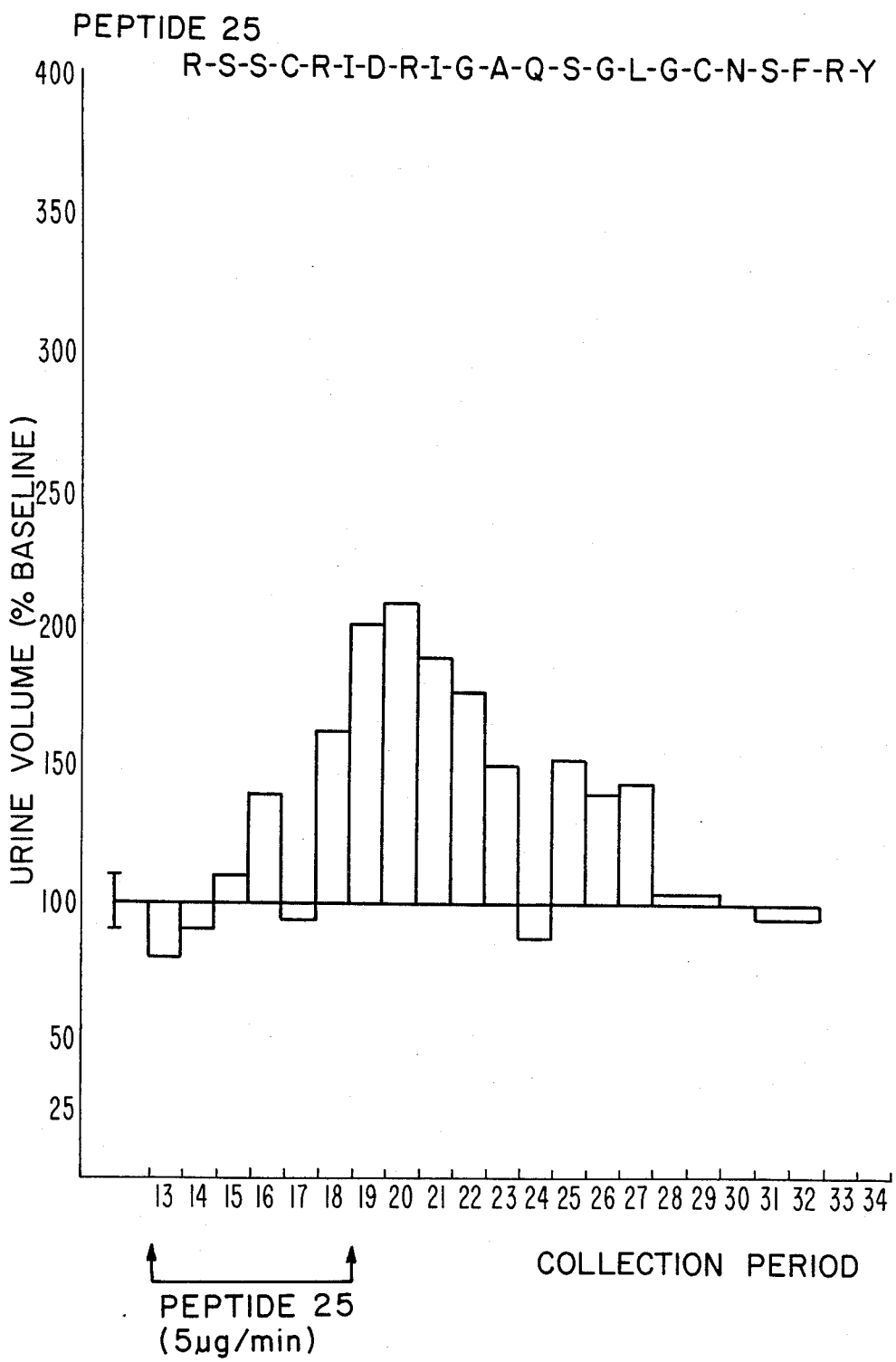

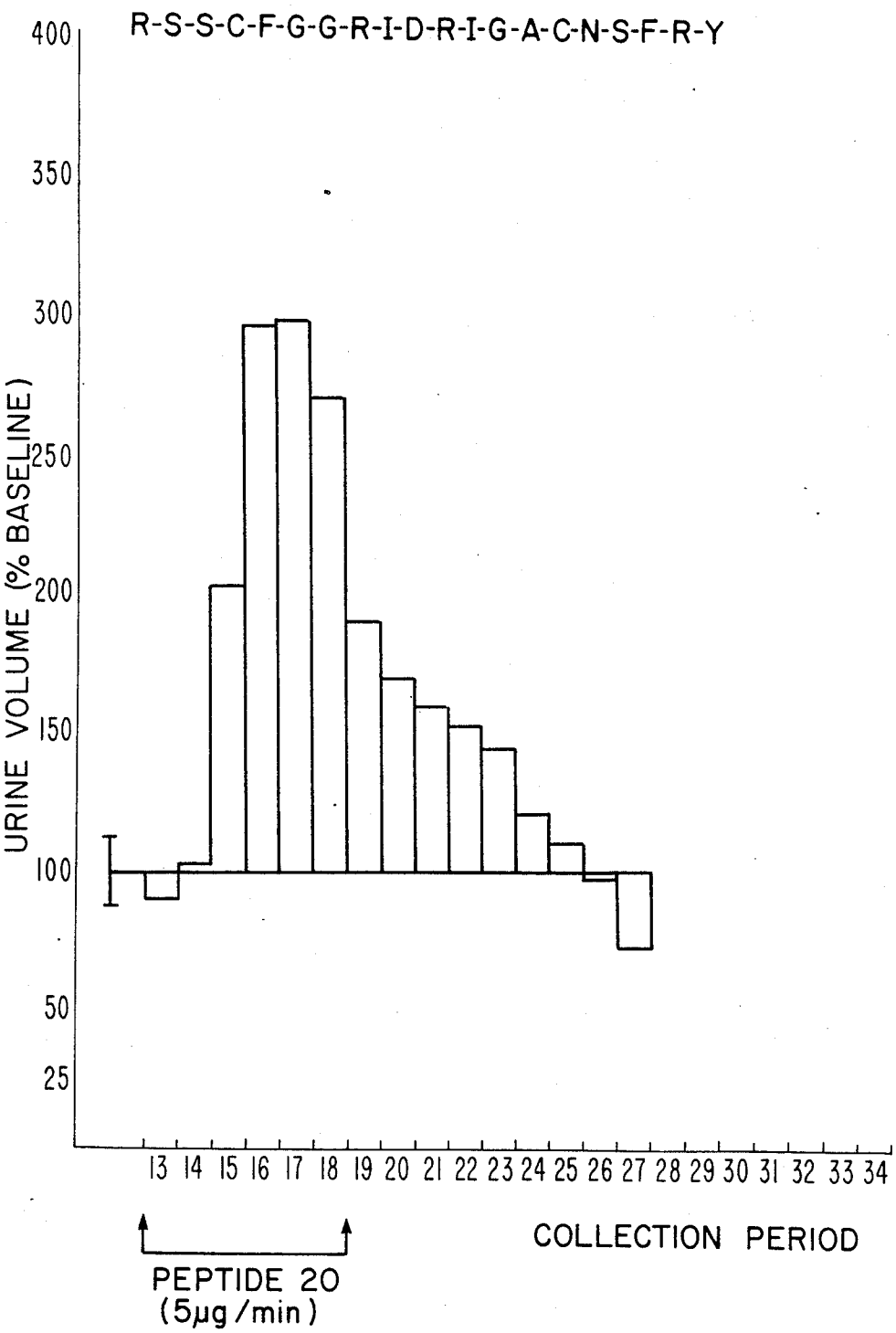

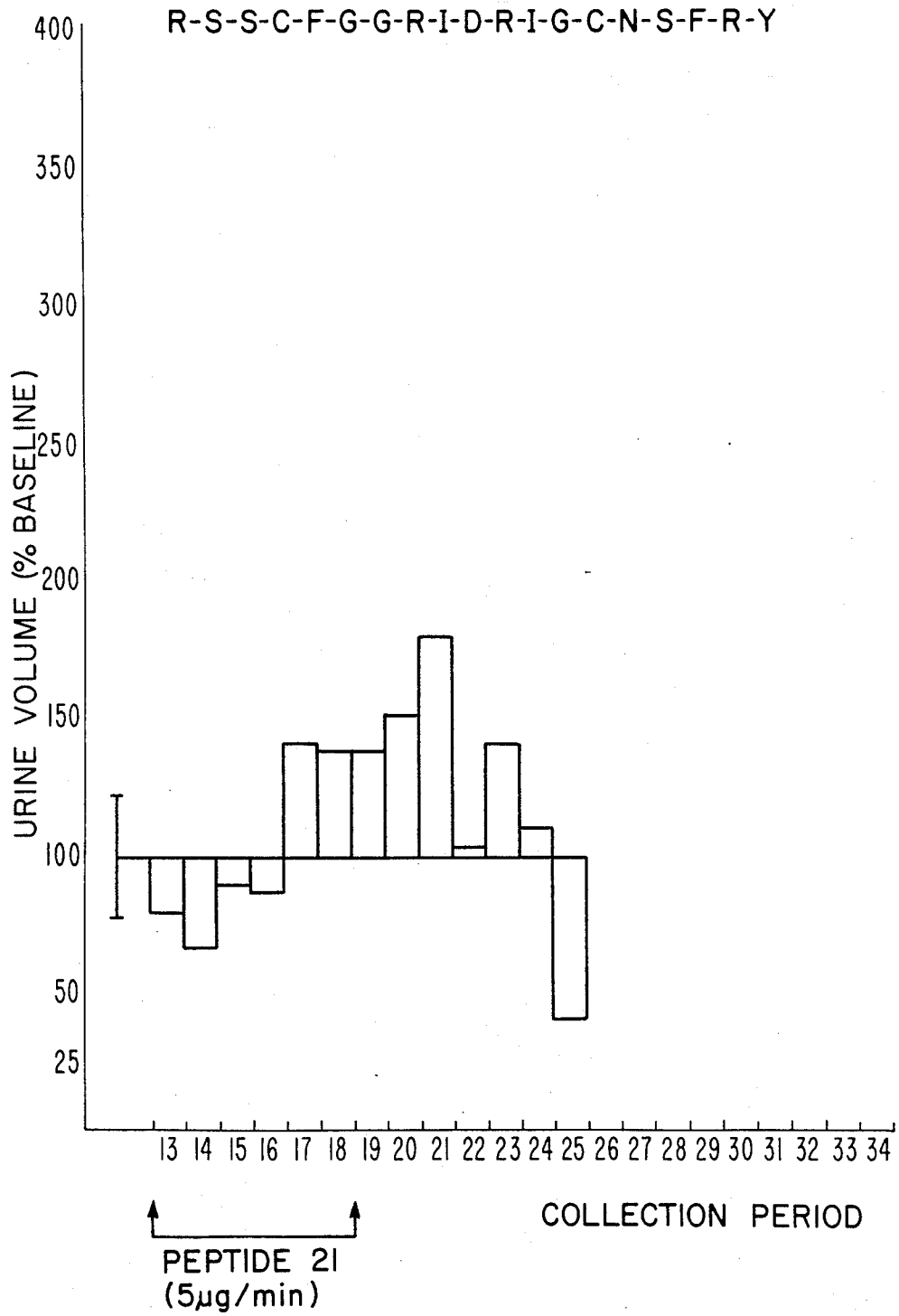

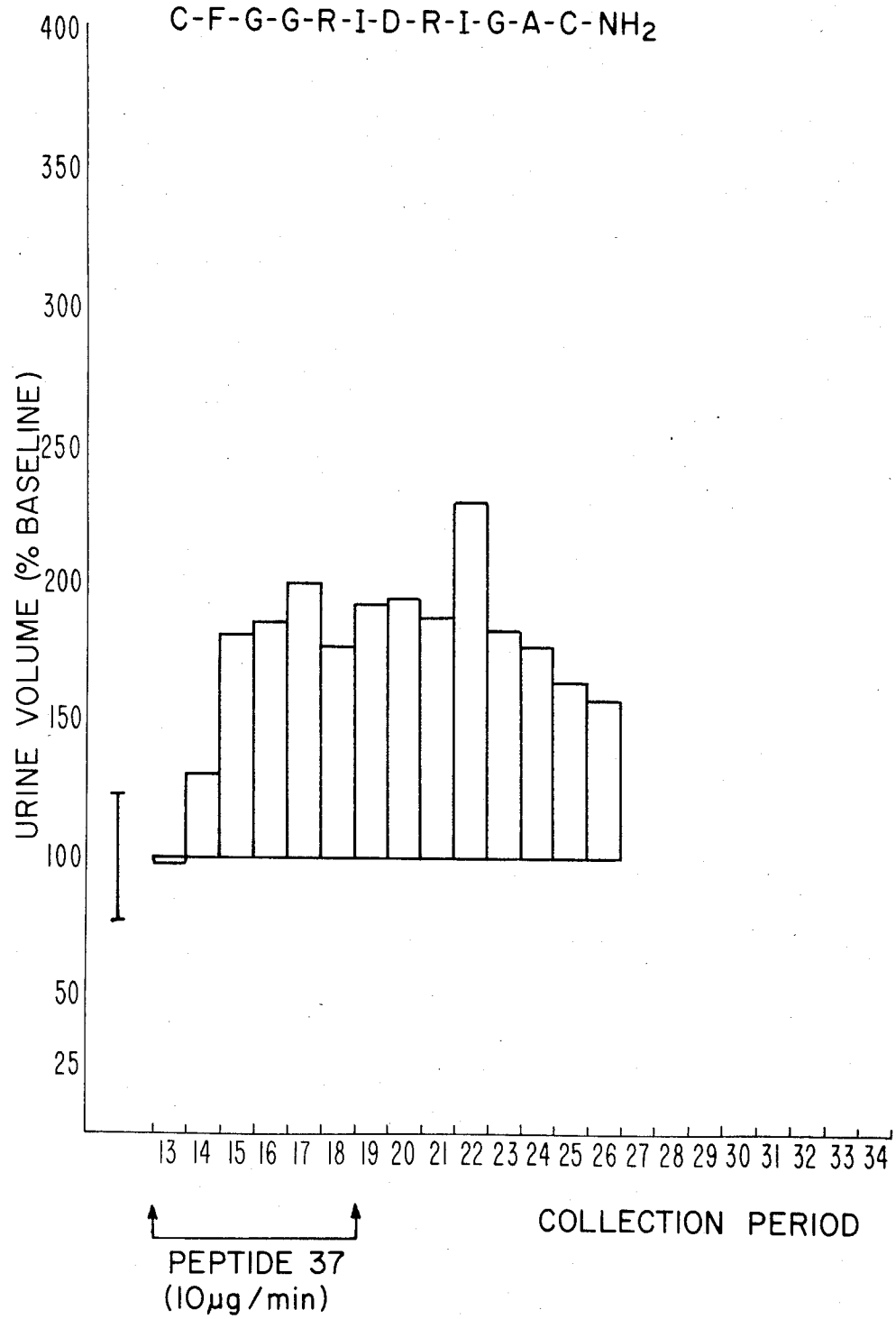

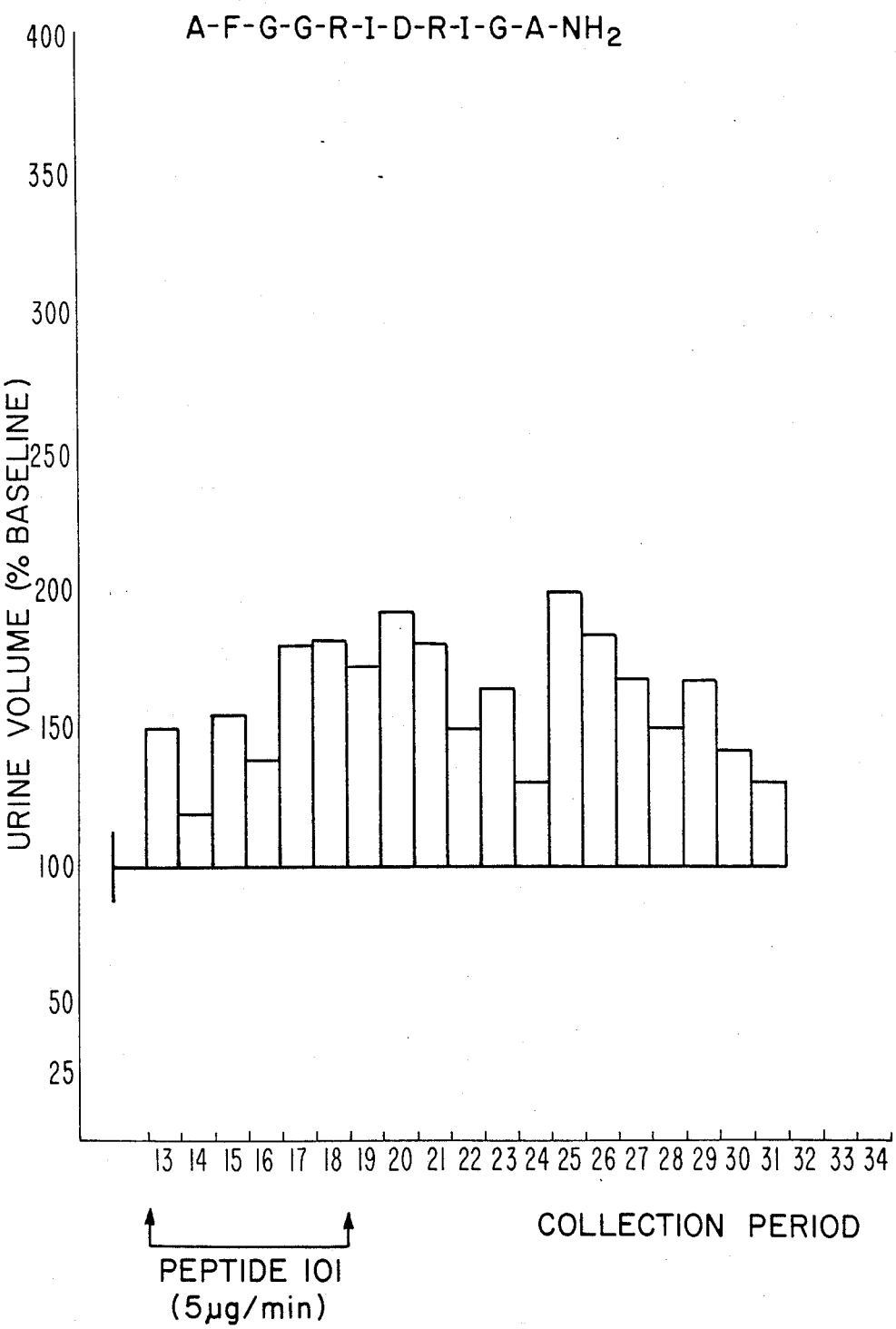

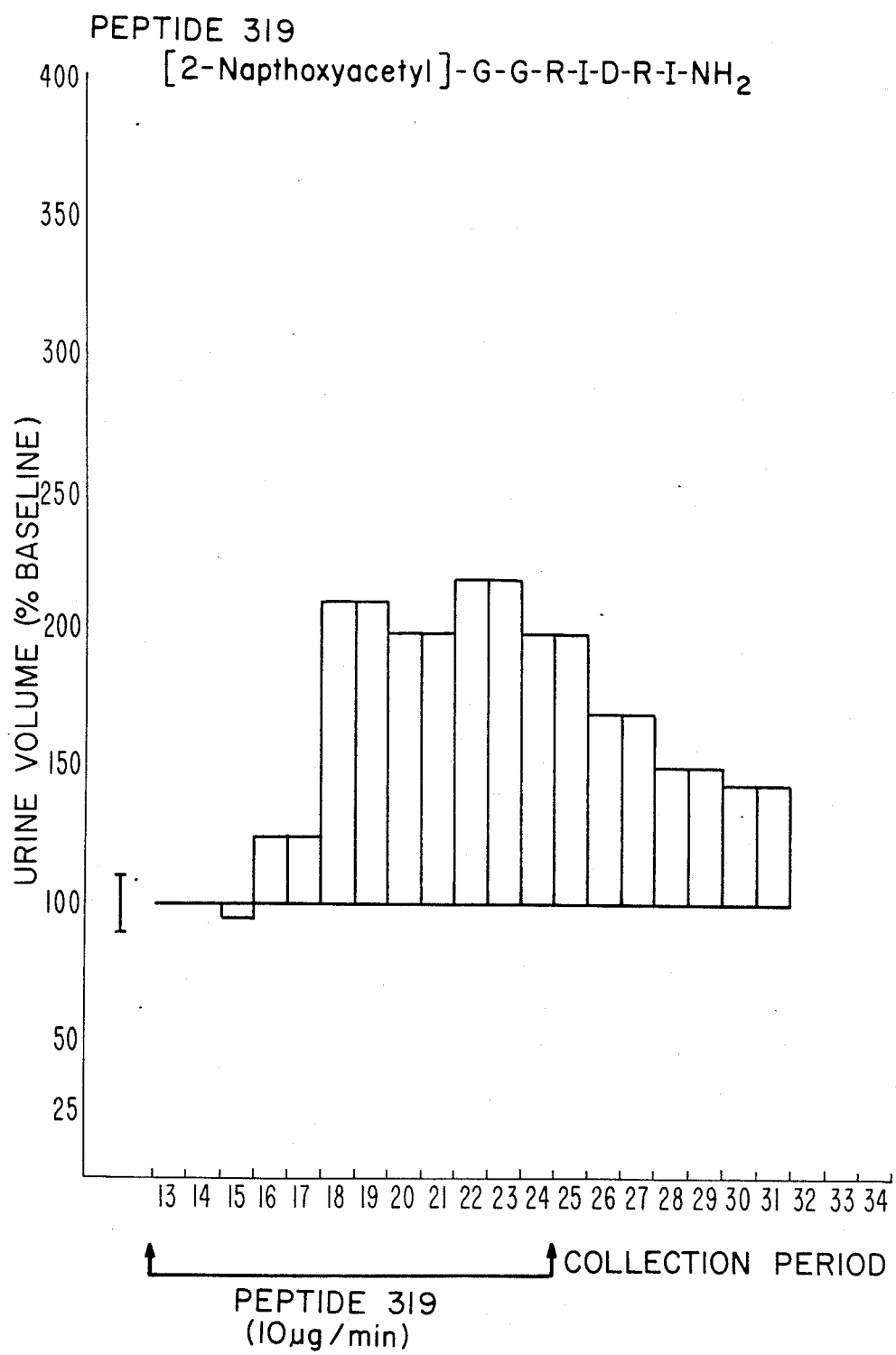

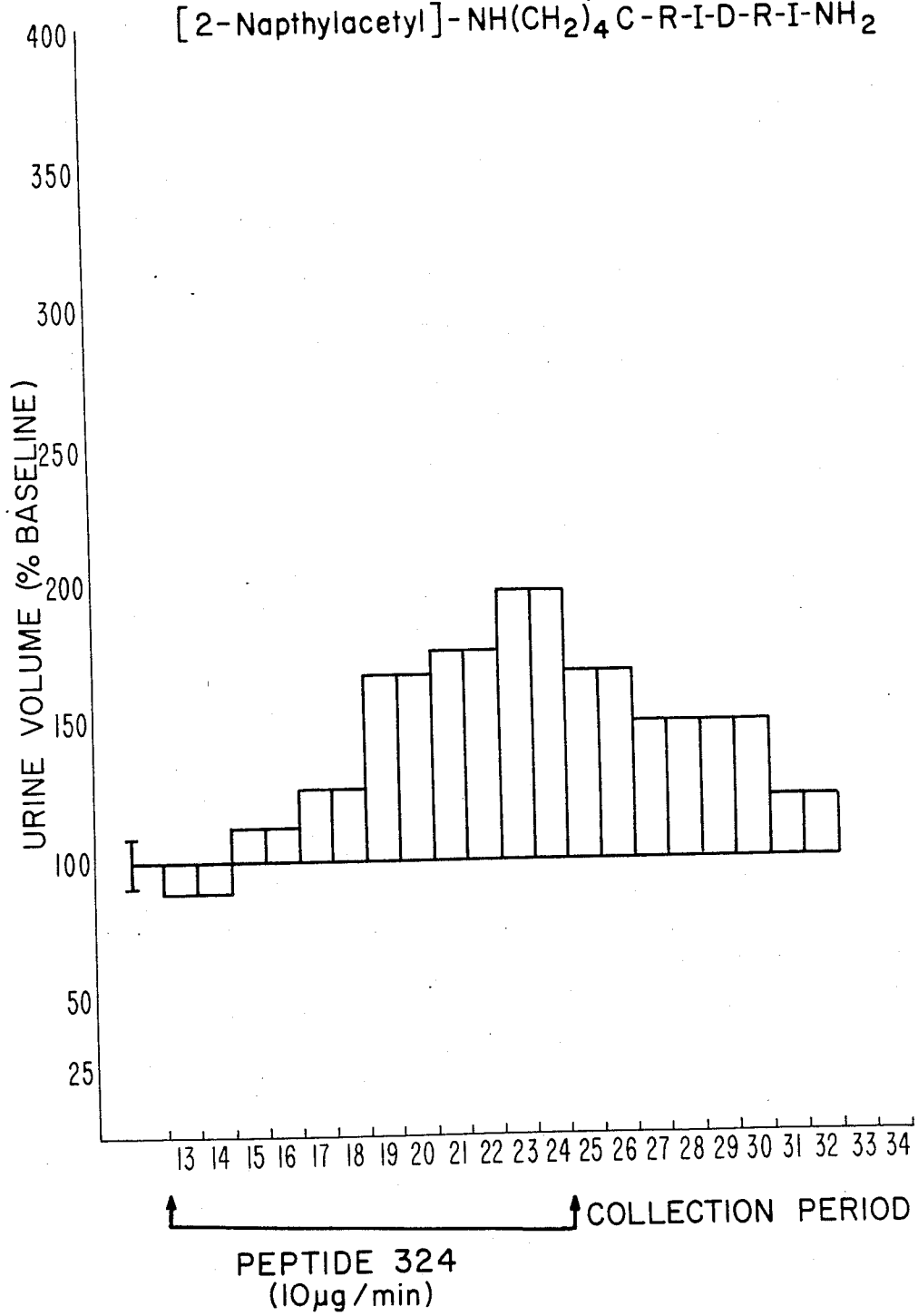

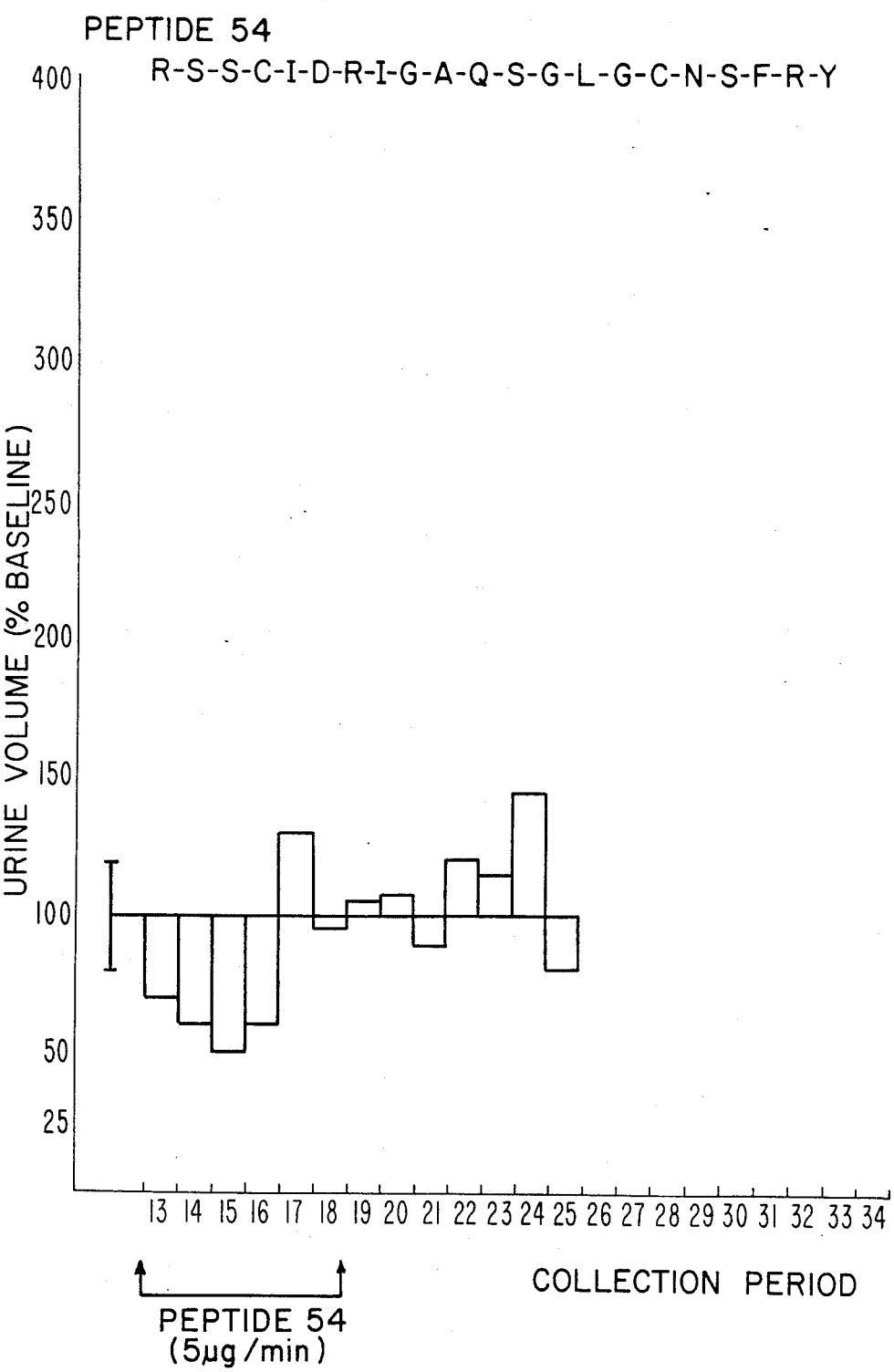

ANALOGS OF ATRIAL NATRIURETIC PEPTIDES

This application is a continuation of application Ser. No. 921,360, filed Oct. 28, 1986, now abandoned.

DESCRIPTION

1. Technical Field

The present invention relates generally to synthetic analogs of atrial peptides and more particularly to synthetic peptide compounds which find use as diuretics, natriuretics and/or vasodilators, or as intermediates for or modulators of such useful compounds, together with methods for their production and use.

2. Background Art

Most multi-cellular organisms are organized into tissues and organs which perform specialized functions. Thus, a system has evolved to transport and circulate materials between them. In higher animals, including mammals, this circulatory system is closed, in order to improve the efficiency of transport. The flow of blood fluid through this closed cardiovascular system requires that the fluid be maintained under pressure and the regulation of the systemic arterial blood pressure requires a complex interaction of numerous factors including, e.g., fluid volume and vascular elasticity and caliber.

The maintenance of normal extracellular fluid volume depends primarily on the excretion of sodium (natriuresis) and water (diuresis) by the kidneys. This is determined by (1) the rate at which plasma is filtered at the glomerulus (glomerular filtration rate, or GFR) and (2) the degree to which sodium is actively reabsorbed along the renal tubule (with water following passively). The latter process is in part regulated by the adrenal steroid hormone aldosterone. It has been long believed that, in addition to GFR and aldosterone, there must be a "third factor" which also regulates sodium reabsorption. It is now apparent that many of the phenomena which required the postulation of a "third factor" can be explained by the effects of physical forces (e.g. blood pressure, red blood cell concentration and plasma viscosity) on sodium reabsorption. Nonetheless, the search continues for a "natriuretic hormone" which might modulate tubular reabsorption.

A natriuretic effect has been demonstrated by crude extracts of rat atrial tissue but not ventricular tissue. De Bold, A. J. et al, Life Sciences, 28: 89–94 (1981), Garcia, R., Experientia, 38: 1071–73 (1982), Currie, M. G. et al., Science 221: 71–73 (1983). Various peptides with diuretic and natriuretic properties have been isolated from atrial tissue and sequenced. Flynn, T. G. et al., Biochem. Biophys. Res. Commun. 117: 859–865 (1983), Currie, M. G. et al., Science 223: 67–69 (1984), Kangawa, K. et al., Biochem. Biophys. Res. Commun. 118: 131–139 (1984).

More recently, various seemingly related peptides have been isolated, sequenced and shown to have natriuretic, diuretic and vasorelaxant activity in varying degrees. U.S. Pat. No. 4,496,544; U.S. Pat. No. 4,508,712; Kangawa, K. et al., Biochem. Biophys. Res. Commun. 121(2): 585–591 (1984); Kangawa, K. et al., Biochem. Biophys. Res. Commun. 119(3): 933–940; Garcia R. et al., Biochem. Biophys. Res. Commun. 126(1): 178–184 (1985); Katsube, N. et al., Biochem. Biophys. Res. Commun. 128(1): 325–330 (1985).

The existence of these atrial natriuretic factors strengthens the long-held suspicion that the heart, aside from its obvious influence on renal perfusion, plays an important role in regulating renal sodium and water excretion.

A number of clinically important disease states are characterized by abnormal fluid volume retention. Congestive heart failure, cirrhosis of the liver and the nephrotic syndrome each lead to excessive fluid accumulation on the venous side of the circulation, the presumed common mechanism being under-perfusion of the kidneys leading to a fall in GFR. In addition the reduced renal perfusion stimulates excessive secretion of renin, a proteolytic enzyme whose action in the circulation leads to the formation of angiotensin. Angiotensin is a powerful constrictor of arterioles (which helps to maintain arterial pressure) and also stimulates release of the sodium-retaining hormone aldosterone by the adrenal gland (which further worsens fluid retention). These mechanisms do not, however, fully account for the fluid retention of the so-called "edematous states", and additional factors are likely to be involved.

An increase in extracellular fluid volume is also thought to contribute to the development of hypertension in many instances. Hypertension, or chronically elevated blood pressure, is one of the major causes of illness and death worldwide. It is estimated that more than 20 million Americans suffer from this disease whose complications include heart failure, heart attack, stroke and kidney failure. The major observed hemodynamic abnormality in chronic hypertension is increased resistance to the flow of blood through the arterioles. The mechanisms which lead to this increased "peripheral resistance" are, however, incompletely understood. In some cases inappropriate activity of the renin-angiotensin system or sympathetic nervous system may lead to excessive constriction of the arterioles; by "inappropriate" it is meant that the unknown signal(s) leading to this activity are not based upon a physiological need of the organism and thus lead to elevated blood pressure. In a substantial fraction of hypertensives however, inappropriate sodium and volume retention by the kidney is felt to either initiate or contribute to the elevated blood pressure. The responsible defect in kidney function and the mechanism whereby fluid retention leads to increased peripheral resistance are both unknown. It is possible that a relative deficiency of a natriuretic hormone could be responsible for these observations, particularly if the same substance also normally exerted a relaxant effect on arterioles.

Diuretic therapy is currently a mainstay in the treatment of hypertension, renal failure and the various edematous states (heart failure, etc.). Currently available pharmacological preparations have, however, several important limitations and undesirable effects. While their use may be directed at a specific abnormality (i.e. volume expansion), their multiple actions are undoubtedly not physiological, leading for instance to potassium depletion, increased retention of uric acid and abnormal glucose and lipid metabolism. In addition, all known diuretics profoundly stimulate the renin-angiotensin-aldosterone system, which counteracts their volume-depleting and blood pressure-lowering effects and leads to other unwanted effects. It would be desirable to provide a pharmacologically effective compound which can regulate blood pressure by providing a complete but controlled range of physiological responses.

However, the isolation of such compounds from atrial tissue is typically a cumbersome process and requires substantial substrate tissue to produce minute quantities of the compounds.

Furthermore, it is considered desirable to provide modifications to the native structures reported for these atrial natriuretic factors in order to isolate the regions of the peptides responsible for the distinct biological activities or regions important in the metabolism and clearance of the peptide. Having determined the appropriate units of activity, structural analogs can be created which preserve. e.g., natriuretic or diuretic activity while decreasing or eliminating vasorelaxant activity. Furthermore, shortened peptide sequences will provide active synthetic analogs which can be taken orally or delivered intranasally to provide the therapeutic benefits of the native compositions.

Shortened and modified peptide sequences will also desirably be formulated to enhance their direct or indirect biological activity, resistance to degradation, biological half-life and to enable the chemosynthetic production of these compounds in a cost effective manner for clinical use.

DISCLOSURE OF THE INVENTION

It has now been found that a class of synthetic analogs of native Atrial Natriuretic Peptides (ANPs) which have been prepared in accordance with the present invention is capable of exhibiting or modulating the natriuretic, diuretic and/or vasorelaxant activity of the native peptides in mammals in vivo.

The synthetic analog compounds of the present invention retain a core pentapeptide sequence of amino acid residues which correspond in a defined way to the sequence $AA_8$-$AA_{12}$ of native ANPs, using the identification system from Atlas, S. et al., Nature 309: 717–719 (1984) wherein the Amino-terminal arginine residue is at position 1. In the known native ANPs, this core sequence is RIDRI in rat and RMDRI in human. Certain defined permutations of this sequence retain activity in vivo and demonstrate that the core peptide structure is a significant factor in the peptides' biological activity.

The present invention is, therefore, in one aspect directed to analog peptide compounds having natriuretic, diuretic and/or vasorelaxant activity in mammals which are identified by the formula:

$$Z_1\text{-}AA_8\text{-}AA_9\text{-}AA_{10}\text{-}AA_{11}\text{-}AA_{12}\text{-}Z_2$$

wherein:
each of $AA_8$ and $AA_{11}$ is, independently, a basic/non-cyclic or neutral/non-polar/small or neutral/polar/non-cyclic amino acid residue:
each of $AA_9$ and $AA_{12}$ is, independently, a neutral/nonpolar/large/non-cyclic amino acid residue, including the D or L optical isomers thereof;
$AA_{10}$ is an acidic amino acid residue; and
wherein the peptide compound is selected from the group consisting of:
(1) compounds wherein $Z_1$ has the formula $Y_1$-$Y_2$,
wherein $Y_1$ is a peptide of from 1 to 125 amino acids having as its Carboxy-terminal residue a hydrophobic amino acid residue, or the desNH$_2$ form thereof, or is a hydrophobic substituent group of the formula

wherein $R_1$ is a hydrophobic aliphatic, aromatic, or mixed aliphatic/aromatic organic group of from 6 to 20 carbon atoms, including groups having substitutions of nitrogen, oxygen or sulfur atoms as amido, thio or oxy; and
$Y_2$ is a spacer group which is an amino acid or dipeptide, or, alternatively, includes a compound of the general formula:

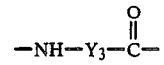

wherein $Y_3$ is preferably a saturated alkyl carbon chain of from 3 to 6 carbon atoms, e.g., $(CH_2)_n$ where n is 3 to 6; and
$Z_2$ is $NH_2$, $NHR'$ or $NR'R''$ wherein R' or R'' are each independently straight or branched chain alkyl of 1–6 carbon atoms, or is a peptide residue of 1–20 amino acid residues, or an amide or alkyl amide thereof; and
(2) compounds wherein $Z_1$ and $Z_2$ taken together form a bridge, and wherein
$Z_1$ has the formula $X_1$-$AA_4$-$X_2$ in which
$X_1$ is a peptide of from 0 to 125 amino acid residues, or the desNH$_2$ form thereof and
$X_2$ is a bond, an amino acid or oligopeptide of up to 10 residues, more usually 4 and preferably 3 or fewer amino acid residues; and
$Z_2$ has the formula $X_3$-$AA_{20}$-$X_4$ in which
$X_3$ is a bond, an amino acid or oligopeptide of up to 10 residues, more usually 7 and preferably 5 or fewer amino acid residues and
$X_4$ is an amino acid or oligopeptide of from 0 to 20 residues, more usually 12 and preferably 8 or fewer amino acid residues, including the Carboxy-terminal amide or alkylamide forms thereof; and
$AA_4$ and $AA_{20}$ are amino acids which together form a bridging bond selected from the group consisting of disulfide bonds, methylene bonds and sulfide/methylene bonds;
with the proviso that:
when $X_2$ is a tripeptide, $X_3$ is not a heptapeptide; and
when $X_2$ is less than a tripeptide, $X_3$ is a least a pentapeptide; and
when $X_1$ is [D-S]-S or S-S, and $X_3$ is an oligopeptide with G-A-Q-S or A-Q-S at the amino-terminus, then $X_4$ cannot be an oligopeptide of less than 6 amino acid residues with N-S at the amino-terminus.

Also provided in accordance with aspects of the invention are pharmaceutical compositions useful as natriuretics, diuretics, vasodilators and/or modulators of the renin-angiostensin-aldosterone system, which compositions containing the above-recited analog peptide compounds, including their amides and esters, and the nontoxic addition salts thereof, together with a pharmaceutically acceptable liquid, gel or solid carrier. Administration of therapeutically effective doses of these compositions can provide effective delivery of the above-recited biological activities to mammalian hosts.

Additional aspects of the present invention provide methods for producing such compounds and compositions, and methods for using the compounds and compositions as therapeutic agents.

BRIEF DESCRIPTION OF THE DRAWINGS

FIG. 1 is a graph which depicts competitive displacement receptor binding of compounds of the present invention using cultured bovine aortic smooth muscle (BASM) cells; and FIG. 2 depicts the in vivo diuretic activities of selected compounds of the present invention in anesthetized rats, wherein FIG. 2A portrays the diuretic activity of the analog peptide identified as AP25, FIG. 2B portrays the diuretic activity of the analog peptide identified as AP20, FIG. 2C portrays the diuretic activity of the analog peptide identified as AP21, FIG. 2D portrays the diuretic activity of the analog peptide identified as AP37, FIG. 2E portrays the diuretic activity of the analog peptide identified as AP101, FIG. 2F portrays the diuretic activity of the analog peptide identified as AP319, FIG. 2G portrays the diuretic activity of the analog peptide identified as AP324, and FIG. 2H portrays the diuretic activity of the analog peptide identified as AP54.

MODES OF CARRYING OUT THE INVENTION

In accordance with the present invention, a class of novel analogs of native Atrial Natriuretic Peptide (ANP) compounds is provided which is capable of exhibiting or modulating the natriuretic, diuretic and/or vasorelaxant activity of the native peptides in mammals in vivo.

The sequence of amino acid residues of the present synthetic analog compounds, the core pentapeptide, and preferred embodiments thereof, are defined in terms of amino acids of certain characteristics of particular subclasses.

Amino acid residues can be generally subclassified into four major subclasses as follows:

Acidic—i.e., the residue has a negative charge due to loss of H ion at physiological pH and the residue is attracted by aqueous solution so as to seek the surface positions in the conformation of a peptide in which it is contained when the peptide is in aqueous medium.

Basic—i.e., the residue has a positive charge due to association with H ion at physiological pH and the residue is attracted by aqueous solution so as to seek the surface positions in the conformation of a peptide in which it is contained when the peptide is in aqueous medium.

Neutral/non-polar, i.e., the residues are not charged at physiological pH and the residue is repelled by aqueous solution so as to seek the inner positions in the conformation of a peptide in which it is contained when the peptide is in aqueous medium.

Neutral/polar, i.e., the residues are not charged at physiological pH and the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not. To fit the definition of charged, a significant percentage (at least approximately 25%) of the individual molecules are charged at physiological pH.

Amino acid residues can be further subclassified as cyclic or non-cyclic, a self-explanatory classification with respect to the side chain substituent groups of the residues, and as small or large. The residue is considered small if it contains a total of 3 carbon atoms or less. Small residues are, of course, always non-cyclic.

For the naturally occurring protein amino acids, subclassification according to the foregoing scheme is as follows:

Acidic: Aspartic acid and Glutamic acid;
Basic/non-cyclic: Arginine and Lysine;
Basic/cyclic: Histidine;
Neutral/polar/small: Glycine, Serine and Cysteine;
Neutral/polar/large/non-cyclic: Threonine, Asparagine and Glutamine;
Neutral/polar/large/cyclic: Tyrosine;
Neutral/non-polar/small: Alanine;
Neutral/non-polar/large/non-cyclic: Valine, Isoleucine, Leucine and Methionine;
Neutral/non-polar/large/cyclic: Phenylalanine and Tryptophan.

The protein amino acid proline, although within the classification neutral/non-polar/large/cyclic, is not included as an alternative due to its known effects on the secondary conformation of peptide chains.

Certain commonly encountered non-protein amino acids, such as α-aminoisobutyric acid (Aib) and sarcosine (Sar), also fall conveniently into particular categories. Based on the above definition, Sar is neutral/non-polar/small, and Aib is neutral/non-polar/non-cyclic.

The nomenclature used to describe ANP analog compunds of the present invention follows the conventional practice wherein the amino group is presented to the left and the carboxy group to the right of each amino acid residue. In the formulae representing selected specific embodiments of the present invention, the Amino- and Carboxy-terminal groups, although not specifically shown, will be understood to be in the form they would assume at physiologic pH values, unless otherwise specified. In the amino acid structure formulae, each residue is generally represented by a single letter designation, corresponding to the trivial name of the amino acid, in accordance with the following schedule:

| Amino Acid | One-letter Symbol |
|---|---|
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

The non-protein amino acids Aminoisobuytric Acid and Sarcosine are represented by the 3-letter designations Aib and Sar, respectively.

In the present application, the L-form of any amino acid residue having an optical isomer is intended unless otherwise expressly indicated, e.g., by the symbol "[D-AA$_n$]".

Compounds within the scope of the present invention can be obtained by modifying the disclosed formulae in numerous ways, while preserving the activity of the ANP analog compounds thus obtained. For example, while the amino acids of these compounds are normally in the natural L optical isomer form, one or more, usually two or less and preferably one amino acid may be replaced with the optical isomer D form, or a D,L-racemic mixture can be provided in the molecules comprising the peptide compound.

Amino acid residues contained within the compounds, and particularly at the Carboxy- or Amino-terminus, can also be modified by amidation, acetylation or substitution with other chemical groups which can, for example, change the solubility of the compounds without effecting their activity.

In particular, it has been discovered that amide modified analogs of Atrial Natriuretic Peptides are particularly potent and therefore preferred embodiments of the present invention. For example, the Carboxy-terminal residue will have a carbonyl carbon which has been substituted with an amino group to form a Carboxy-terminal amido group. In general, the nitrogen atom of the amido group, covalently bound to the carbonyl carbon, will be of the general formula—NR'R", where R' and R" are substituent groups. Each substituent group can independently be hydrogen, or an organic group such as alkyl, straight chain or branched of from one to ten, usually one to six carbon atoms, including groups having substitutions of three or less nitrogen, oxygen or sulfur atoms as amido, thio or oxy, or a benzylic group (substituted or unsubstituted), and any one of which can be a nitrogen containing moiety such as hydrazide and the other can be hydrogen, or either group can be a basic or neutral dipeptide and the other can be hydrogen or an alkyl group. Representative of such amido groups are: —NH$_2$, —NHCH$_3$, —N(CH$_3$)$_2$ and —NHCH$_2$CH$_3$, among others.

In forming amidated analogs of the present invention, the analog compounds can be synthesized directly, for example using BOC-AA$_x$-pMBHA-Resin or Boc-AA$_x$-BHA-Resin, wherein AA$_x$ is the selected Carboxy-terminal amino acid of the desired analog compound as described in further detail below. Alternatively, the analog compounds of the present invention can be chemically or enzymatically amidated subsequent to peptide synthesis using means well known to the art.

In addition, certain amino acid residues contained within the disclosed compounds, and particularly at the Amino-terminus, can also be modified by deamination, in order to provide resistance to degradation in the host by endogenous peptidase enzyme cleavage. Such deamination can be accomplished in the synthesized compound, for example, by employing L Amino Acid Oxidase (EC 1.4.3.2, derived from the venom of, e.g., *Crolatus atrox*) or D Amino Acid Oxidase (EC 1.4.3.3, derived from, e.g., porcine kidney), which are available commercially (Sigma Chemical Co., St. Louis, MO).

Preferably, deamination can be effectively accomplished by selecting the appropriate α-keto acid as an alternative to the Amino-terminal amino acid residue. For example, the amino acid residues arginine, serine, leucine, cysteine, alanine, phenylalanine and glycine can be replaced with the alternative α-keto acids 5-Guanidino pentanoic acid, 3-Hydroxy propanoic acid, 4-Methyl pentanoic acid, 3-Mercapto propionic acid, Propionic acid, Hydrocinnamic acid and Acetic acid, respectively. Most α-keto acids which correspond to the amino acid residues employed in the present invention are available commercially, e.g., from Aldrich Chemical Co., Inc., Milwaukee, WI. The desired α-keto acid can also be synthesized by means well known to those having ordinary skill in the art of chemical synthesis.

For those compounds of the invention wherein Z$_1$ is Y$_1$-Y$_2$, Y$_1$ may be a large, hydrophobic non-amino acid related moiety of 6–20 carbon atoms, and may be aliphatic or aromatic. Such substituent groups may enhance the stability of the peptide by making it resistant to attack by proteases. The carbon chains or rings therein may be substituted by, and/or may include heteroatoms, such as N, O, or S.

Preferred Embodiments

The compounds of the invention all contain the core sequence:

AA$_8$-AA$_9$-AA$_{10}$-AA$_{11}$-AA$_{12}$ wherein
  each of AA$_8$ and AA$_{11}$ is, independently, a basic/non-cyclic or neutral/non-polar/small or neutral/polar/non-cyclic amino acid residue;
  each of AA$_9$ and AA$_{12}$ is, independently, a neutral/non-polar/non-cyclic amino acid residue in the D or L optical isomer configuration; and
  AA$_{10}$ is an acidic amino acid residue.

The most preferred sequence of this core is R(I/M)DRI, wherein all residues are in the L configuration and the amino acid residues contained within the parentheses are alternatives. Next in preference are those sequences wherein only one of the R(I/M)DRI residues has been substituted by an alternative residue within the above definitions.

Preferred substitutions are:
A, Q, N, or K for R as AA$_8$ or AA$_{11}$;
V, [D-V], L, [D-L], [D-I] or [D-M] for I or M as AA$_9$;
M, [D-M], V, [D-V], L, [D-L], or [D-I] for I as AA$_{12}$; and
E for D as AA$_{10}$.

Particularly preferred are those embodiments wherein this sequence is selected from the group consisting of:

| | | |
|---|---|---|
| A(I/M)DRI, | K(I/M)DRI, | Q(I/M)DRI, |
| RVDRI, | RLDRI, | R[D—I]DRI, |
| R[D—M]DRI, | R(I/M)ERI, | R(I/M)DQI, |
| R(I/M)DKI, | R(I/M)DRM, | R(I/M)DRV, |
| R(I/M)DRL, | R(I/M)DR[D—I], | R(I/M)DR[D—M]. |

More than one alteration from the naturally occurring RIDRI or RMDRI sequence is within the scope of the invention but less preferred. Particularly favored subsets of this group include those wherein the D of AA10 is substituted by E, in addition to another substitution.

The peptides of the invention, which contain the core pentapeptide AA$_8$-AA$_9$-AA$_{10}$-AA$_{11}$-AA$_{12}$, wherein each numbered AA is as above defined fall into two general classes: linear peptides and peptide derivatives; and cyclic peptides, which contain a ring by virtue of a bridging bond, such as a disulfide (i.e., the "cyclic disulfides") or methylene bridge. The cyclic disulfides are the more closely analogous to the naturally occurring ANPs, which contain 17 amino acid residue-member disulfide rings, inclusive of the two C residues which provide the sulfhydryl groups for the formation of the disulfide bond. However, the cyclic disulfide compounds of the invention all contain either more or, much more preferably, less, than 17 amino acid residues in the cyclic structure.

As indicated, certain cyclic analogs of the present invention can also be provided by bonding the cysteine residues, or equivalent residues, with an equivalent bond or linking group such as, for example, —$CH_2$—. The replacement of a sulfhydryl group on the cysteine residue with an alternative group will effectively replace the cysteine residue with an alternative amino acid. For example, replacing the sulfhydryl group with a —$CH_2$— group will convert the residue to the functional equivalent of α-amino butyric acid. These cyclic analog peptides can be formed, for example, in accordance with the methodology of Lebl, M. and V. J. Hruby, Tetrahedron Lett. 25 (20): 2067–2068 (1984) or by employing the procedure disclosed in U.S. Pat. No. 4,161,521.

It appears that the amino acid residues forming the peptides of the invention outside of the region of the pentapeptide core may often be present in either the D or L optical isomer form while retaining activity. This is inclusive of the C residues which can be responsible for the formation of the cyclic structure, as well as the ring members other than the core pentapeptide and the residues outside the ring in the cyclic disulfides, and of the additional peptide sequences other than the core pentapeptide in the linear forms. Therefore, the amino acid designations used in specifying preferred embodiments of these peptides, while intended to designate the L forms, unless otherwise noted, should be understood to imply that the D form could conveniently be substituted therefor. Certain portions of the pentapeptide sequence appear less sensitive to the configuration of the amino acid than others; however, the amino acid residues designated in this core sequence are in the L configuration unless otherwise noted.

Thus, the cyclic peptides of the invention have the formula:

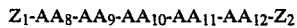

wherein $Z_1$ and $Z_2$ together form a bridge, and
wherein $Z_1$ has the formula $X_1$-$AA_4$-$X_2$ in which
  $X_1$ is a peptide of from 0 to 125 amino acid residues, or the desNH$_2$ form thereof and
  $X_2$ is a bond, an amino acid or oligopeptide of up to 10 residues, more usually 4 and preferably 3 or fewer amino acid residues; and
wherein $Z_2$ has the formula $X_3$-$AA_{20}$-$X_4$ in which
  $X_3$ is a bond, an amino acid or oligopeptide of up to 10 residues, more usually 7 and preferably 5 or fewer amino acid residues and
  $X_4$ is an amino acid or oligopeptide of up to 20 residues, more usually 10 and preferably 5 or fewer amino acid residues, including the Carboxy-terminal amide or alkylamide forms thereof; and
$AA_4$ and $AA_{20}$ are amino acids which together form a bridging bond selected from the group consisting of disulfide bonds, methylene bonds and sulfide/methylene bonds, with the proviso that:

when $X_2$ is a tripeptide, $X_3$ is not a heptapeptide; and
when $X_2$ is less than a tripeptide, $X_3$ is a least a pentapeptide; and
when $X_1$ is [D-S]-S or S-S, and $X_3$ is an oligopeptide with G-A-Q-S or A-Q-S at the amino-terminus, then $X_4$ cannot be an oligopeptide of less than 6 amino acid residues with N-S at the amino-terminus.

Preferred embodiments for $Z_1$ include those wherein $X_1$ is a peptide of 0–6 amino acid residues, generally of the form $AA_{-3}$-$AA_{-2}$-$AA_{-1}$-$AA_1$-$AA_2$-$AA_3$, wherein
  $AA_{-3}$ and $AA_{-2}$ are neutral/polar/small or neutral/non-polar/small,
  $AA_3$ is neutral/polar/small, neutral/polar/cyclic or neutral/non-polar/small,
  $AA_{-2}$ is neutral/non-polar/non-cyclic, and
  $AA_{-1}$ and $AA_1$ are basic/non-cyclic, and truncated forms thereof.

In particular, preferred embodiments for $X_1$ are those peptides selected from the group consisting of:
  S-L-R-R-S-S, L-R-R-S-S, R-R-S-S, R-S-S, S-S, S, R, Y and desX$_1$.

Preferred embodiments for $Z_1$ also include those wherein $X_2$ is a peptide of 0–3 amino acid residues, of the general formula $AA_5$-$AA_6$-$AA_7$, and truncated forms thereof, wherein
  $AA_5$ is neutral/non-polar/large/cyclic, neutral/non-polar/small or neutral/polar/small, and
  $AA_6$ and $AA_7$ are neutral/polar/small, neutral/non-polar/large/non-cyclic, basic/non-cyclic or neutral/non-polar/small.

In particular, preferred embodiments for $X_2$ are those peptides wherein the amino acid residues are selected from the group consisting of G, F, A, S, L, V, Sar and Aib, and the peptides are selected from the group consisting of:
  F-G-G, (desNH$_2$-F)-G-G, [D-F]-G-G, F-G-A, F-A-G, F-[D-A]-G, F-[D-S]-G, F-[D-L]-G, F-[D-V]-G, [D-F]-G-G, [D-A]-G-G, F-G-[D-A], F-Aib-G, A-G-G, F-G, G-G, [D-A]-G, [D-S]-G, G-[D-A], G-[Aib], G-[Sar], G and desX$_2$.

Preferred embodiments of $Z_2$ in the cyclic forms of the peptides of the invention include those wherein $X_3$ is a peptide containing 0–7 amino acid residues, generally peptides of the form
  $AA_{13}$-$AA_{14}$-$AA_{15}$-$AA_{16}$-$AA_{17}$-$AA_{18}$-$AA_{19}$, or the truncated forms thereof, wherein
  $AA_{13}$, $AA_{16}$, $AA_{17}$ and $AA_{19}$ are neutral/polar/small;
  $AA_{14}$ is neutral/non-polar/small;
  $AA_{15}$ is neutral/polar/large/non-cyclic; and
  $AA_{18}$ is neutral/non-polar/large/non-cyclic.

In particularly preferred embodiments, the amino acid residues are selected from G, A, Q, S, and L, and still more preferred, the peptides are selected from the group consisting of:
  G-A-Q-S-G-L-G, G-A-Q-S-G-L, A-Q-S-G-L-G, G-A-Q-S-G, Q-S-G-L-G, G-A-Q-S, S-G-L-G, G-A-Q, G-A-A, G-L-G, L-G, G-A, G and desX$_3$.

Preferred embodiments for $Z_2$ also include those wherein $X_4$ is NH$_2$, or a peptide of 0–5 amino acid residues, and the amide or alkylamide forms thereof, wherein the amino acids are selected from N, S, F, R, and Y, and in particularly preferred embodiments, the peptide is selected from
  N-S-F-R-Y, N-S-F-R, N-S-R, N-S, N or desX$_4$ and the amides thereof.

For the linear forms of the peptides of the invention, $Z_1$ has the formula $Y_1$-$Y_2$, wherein $Y_1$ is a peptide of from 1 to 125 amino acids having as its Carboxy-terminal residue a hydrophobic amino acid residue, or the desNH$_2$ form thereof, or is a hydrophobic substituent group of the formula

wherein
- $R_1$ is a hydrophobic aliphatic, aromatic, or mixed aliphatic/aromatic organic group of from 6 to 20 carbon atoms, including groups having substitutions of nitrogen, oxygen or sulfur atoms as amido, thio or oxy; and
- $Y_2$ is a spacer group which is an amino acid or dipeptide, or, alternatively, includes a compound of the general formula:

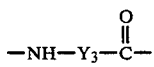

wherein
- $Y_3$ is preferably a saturated alkyl carbon chain of from 3 to 6 carbon atoms, e.g., $(CH_2)_n$ where n is 3 to 6; and
- $Z_2$ is NH$_2$, NHR$_4'$ or NR'R'' wherein R' or R'' are independently straight or branched chain alkyl of 1-6 carbon atoms, or a peptide residue of 1-20 amino acid residues, or an amide or alkyl amide thereof.

Preferred forms of $Y_1$ include peptides of 1-5, more usually 1-3 amino acids or the desNH$_2$ forms thereof, wherein the C-terminal amino acid is neutral/non-polar/cyclic, and most particularly is F or desNH$_2$-F. For $Y_1$ of the form AA$_3$-AA$_4$-AA$_5$, preferred embodiments for AA$_3$ and AA$_4$ include neutral/polar amino acids, and neutral/non-polar/small amino acids. Most preferred are YAF, RCF, SCF, AF, CF, and F or desNH$_2$-F.

Preferred non-peptide derived forms of $Y_1$ include organic substituent groups which are generally non-toxic, hydrophobic and relatively large or bulky when compared to substituent groups ordinarily found with amino acid residues.

Presently preferred organic substituent groups can be represented by the general formula:

wherein $R_1$ is an organic group containing at least three carbon atoms. Included in this formula are 2-substituted acetyl and 3-substituted propionyl groups, and 4-substituted butyryl groups, wherein the substitutions to these groups include the general class of neutral, hydrophobic mono- and polycyclic aromatic or saturated ring systems. Representative examples of the presently preferred substituent groups (shown as if bonded to the present peptides) include:

fluorenylmethyloxycarbonyl (FMOC)

-continued

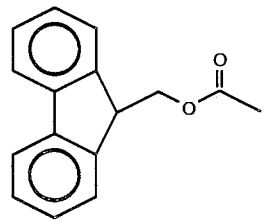

benzyloxycarbonyl (CBZ)

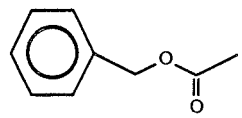

Diphenylpropionyl

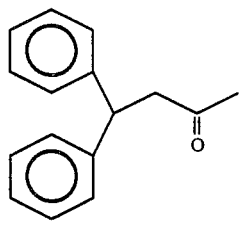

Triphenylpropionyl

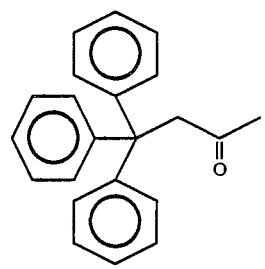

3-Indolepropionyl

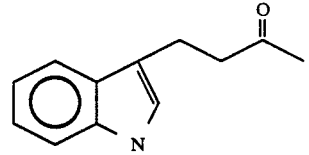

4-Indolebutyryl

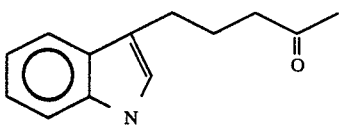

1-Adamantylacetyl

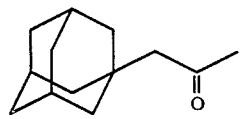

1-Napthylacetyl

-continued

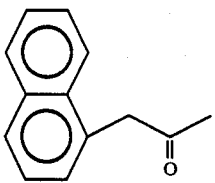

2-Napthylacetyl

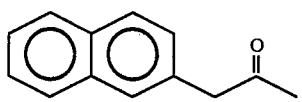

1-Napthoxyacetyl

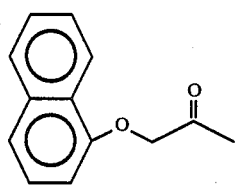

and

2-Napthoxyacetyl

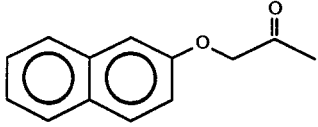

In addition to embodiments where $Y_2$ is

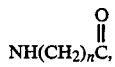

where n is 3 to 6, preferred forms include dipeptides $AA_6$-$AA_7$, wherein $AA_6$ and $AA_7$ are the same or different and are preferably neutral/polar/small, most preferably G.

Preferred forms of $Z_2$ are of the form $X_3$-$AA_{20}$-$X_4$, wherein $X_3$ and $X_4$ have the same definitions and preferred embodiments as above, and wherein $AA_{20}$ is neutral/non-polar/small or neutral/polar/small, preferably C or A. Additional particularly preferred forms of $Z_2$ are —$NH_2$ and —NHR', as defined above.

Compounds within the scope of the present invention can be synthesized chemically by means well-known in the art such as, e.g., solid phase peptide synthesis. The synthesis is commenced from the Carboxy-terminal end of the peptide using an alpha-amino protected amino acid. t-Butoxycarbonyl (Boc) protective groups can be used for all amino groups even though other protective groups are suitable. For example, Boc-N-OH, Boc-S-OH, Boc-F-OH, Boc-R-OH or Boc-Y-OH (i.e., selected ANP analog Carboxy-terminal amino acids) can be esterified to chloromethylated polystyrene resin supports. The polystyrene resin support is preferably a copolymer of styrene with about 0.5 to 2% divinyl benzene as a cross-linking agent which causes the polystyrene polymer to be completely insoluble in certain organic solvents. See Stewart et al., Solid-Phase Peptide Synthesis, W. H. Freeman Co., San Francisco (1969) and Merrifield, J. Am. Chem. Soc. 85: 2149–2154 (1963). These and other methods of peptide synthesis are also exemplified by U.S. Pat. Nos. 3,862,925, 3,842,067, 3,972,859 and 4,105,602.

In the synthesis of those compounds which include an Amino-terminal α-keto acid bound to the sequence of amino acid residues, the appropriate α-keto acid can generally be added without employing the protecting groups ordinarily used with amino acid residues. However, succinic acid and glutaric acid (the α-keto acids corresponding to aspartic acid and glutamic acid, respectively) will generally be incorporated by employing the ½ benzyl derivative of the α-keto acid.

Conveniently, compounds may be synthesized using manual techniques or automatically employing, for example, an Applied BioSystems 430A Peptide Synthesizer (Foster City, Calif.) or a Biosearch SAM II automatic peptide synthesizer (Biosearch, Inc. San Rafael, Calif.), following the instructions provided in the instruction manual supplied by the manufacturer.

It will be readily appreciated by those having ordinary skill in the art of peptide synthesis that the intermediates which are constructed in accordance with the present disclosure during the course of synthesizing the present analog compounds are themselves novel and useful compounds and are thus within the scope of the invention.

Alternatively, selected compounds of the present invention can be produced by expression of recombinant DNA constructs prepared in accordance with well-known methods. Such production can be desirable to provide large quantities or alternative embodiments of such compounds.

Compounds of the present invention are shown to have natriuretic, diuretic and hypotensive activity in the intact mammal. Furthermore, compounds of the present invention including synthetic compounds, may possess vasorelaxant activity or inhibit the release of aldosterone.

Compounds of the present invention, in linear or cyclic ring form, which are shown to have the above recited physiological effects can find use in numerous therapeutical applications such as, e.g., inducing natriuresis, diuresis, and vasodilatation. Thus these compounds, and compositions containing them, can find use as therapeutic agents in the treatment of various edematous states such as, for example, congestive heart failure, nephrotic syndrome and hepatic cirrhosis, in addition to hypertension and renal failure due to ineffective renal perfusion or reduced glomerular filtration rate.

Thus the present invention also provides compositions containing an effective amount of compounds of the present invention, including the nontoxic addition salts, amides and esters thereof, which may, alone, serve to provide the above-recited therapeutic benefits. Such compositions can also be provided together with physiologically tolerable liquid, gel or solid diluents, adjuvants and excipients.

These compounds and compositions can be administered to mammals for veterinary use, such as with domestic animals, and clinical use in humans in a manner similar to other therapeutic agents. In general, the dosage required for therapeutic efficacy will range from about 0.01 to 1000 μg/kg, more usually 0.1 to 1000 μg/kg of the host body weight. Alternatively, dosages within these ranges can be administered by constant infusion over an extended period of time, usually exceeding 24 hours, until the desired therapeutic benefits have been obtained.

Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiological tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10% preferably 1%–2%. Oral formulations include such normally employed excipients as, for example, pharmaceutical grades of mannitol, lactose, starch, magnesium stearate, sodium saccharin, cellulose, magnesium carbonates, and the like. These compositions take the form of solutions, suspensions, tablets, pills, capsules, sustained release formulations, or powders, and contain 10%–95% of active ingredient, preferably 25%–70%.

The peptide compounds may be formulated into the compositions as neutral or salt forms. Pharmaceutically acceptable non-toxic salts include the acid addition salts (formed with the free amino groups) and which are formed with inorganic acids such as, for example, hydrochloric or phosphoric acids, or such organic acids such as, for example, hydrochloric or phosphoric acids, or such organic acids as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In addition to the compounds of the present invention which display natriuretic, diuretic or vasorelaxant activity, compounds of the present invention can also be employed as intermediates in the synthesis of such useful compounds. Alternatively, by appropriate selection, compounds of the present invention whose activity levels are reduced or eliminated entirely can serve to modulate the activity of other diuretic, natriuretic or vasorelaxant compounds, including compounds outside the scope of the present invention, by, for example, binding to alternate receptors, stimulating receptor turnover, or providing alternate substrates for degradative enzyme or receptor activity and thus inhibiting these enzymes or receptors. When employed in this manner, such compounds can be delivered as admixtures with other active compounds or can be delivered separately, for example, in their own carriers.

Compounds of the present invention can also be used for preparing antisera for use in immunoassays employing labelled reagents, usually antibodies. Conveniently, the polypeptides can be conjugated to an antigen by means of dialdehydes, particularly from 4 to 6 carbons atoms and aliphatic, or carbodiimide. These compounds and immunologic reagents may be labelled with a variety of labels such as chromophores, fluorophores such as, e.g., fluorescein or rhodamine, radioisotopes such as $^{125}I$, $^{35}S$, $^{14}C$, or $^{3}H$, or magnetized particles, by means well known in the art.

These labeled compounds and reagents, or labeled reagents capable of recognizing and specifically binding to them, can find use as, e.g., diagnostic reagents. Samples derived from biological specimens can be assayed for the presence or amount of substances having a common antigenic determinant with compounds of the present invention. In addition, monoclonal antibodies can be prepared by methods known in the art, which antibodies can find therapeutic use, e.g., to neutralize overproduction of immunologically related compounds in vivo.

The following examples are provided by way of illustration, rather than implying any limitation of the subject invention.

EXPERIMENTAL

In the experimental disclosure which follows, the amino acid sequence of chemically synthesized ANP analog compounds are numbered from the Amino-terminal arginine residue corresponding to the arginine residue found at position 1 in the native rat-derived Atrial Natriuretic Peptide sequence disclosed in Atlas, S. et al., Nature 309: 717–719 (1984).

I. Chemical Synthesis of Atrial Natriuretic Peptide Analog Compounds

A. Synthesis Procedures

Compounds of the present invention having the general formula:

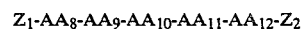

$$Z_1\text{-}AA_8\text{-}AA_9\text{-}AA_{10}\text{-}AA_{11}\text{-}AA_{12}\text{-}Z_2$$

wherein:
  each of $AA_8$ and $AA_{11}$ is, independently, a basic/non-cyclic or neutral/non-polar/small or neutral/polar/non-cyclic amino acid residue:
  each of $AA_9$ and $AA_{12}$ is, independently, a neutral/nonpolar/large/non-cyclic amino acid residue, including the D or L optical isomers thereof;
  $AA_{10}$ is an acidic amino acid residue; and
wherein $Z_1$ and $Z_2$ are as previously defined have been prepared in order to illustrate the present invention. The compounds were synthesized by solid-phase techniques performed manually or, alternatively, on an Applied BioSystems 430A Peptide Synthesizer (Foster City, Calif.) or a Biosearch SAM II automated peptide synthesizer (Biosearch, San Rafael, Calif.) using t-Boc amino acids in accordance with the instructions of the manufacturer.

In accordance with the above description, the following procedures were used for the chemical synthesis of novel analog ANP compounds.

Procedure A

Preparation of Boc-$AA_1$ ... $AA_{n-1}$-$AA_n$-Resin Hydroxymethyl Polystyrene Ester One gram of selected Boc-$AA_n$-O-Polystyrene-Resin (0.2–0.6 mmole/g resin) (obtainable from, e.g., Peninsula Labs, Inc.) is treated according to schedule A for incorporation of the Boc-$AA_{n-1}$-OH.

Schedule A (1) Wash 3× with dichloromethane ($CH_2Cl_2$);

(2) Treat for 1 min. with TFA:CH$_2$Cl$_2$:ethane dithiol (EDT) (45:50:5 by volume);
(3) Treat for 20 min. with TFA:CH$_2$Cl$_2$:EDT (45:50:5) by volume;
(4) Wash 3× with CH$_2$Cl$_2$;
(5) Treat 2× for 1 min. 10% (V/V) Diisopropylethylamine (DIPEA) in CH$_2$Cl$_2$;
(6) Wash 2× with CH$_2$Cl$_2$;
(7) Wash 2× with methanol (MeOH);
(8) Repeat (5-7) once;
(9) Wash 3× with CH$_2$Cl$_2$;
(10) Add 1-6 equivalents of preformed symmetrical anhydride of the suitably protected Boc-amino acid dissolved in CH$_2$Cl$_2$ or dimethyl formamide (DMF)/CH$_2$Cl$_2$ (50:50 volume) (Boc-N-OH, Boc-Q-OH and Boc-R(TOS)-OH were coupled as active esters using N-hydroxybenzotriazole);
(11) Wash 2× with CH$_2$Cl$_2$;
(12) Wash 2× with 10% DIPEA;
(13) Wash 2× with CH$_2$Cl$_2$;
(14) Wash 2× with MeOH;
(15) Wash 2× with CH$_2$Cl$_2$;
(16) Repeat steps (11-15) once;
(17) Test by ninhydrin reaction according to Kaiser et al., Anal. Biochem. 34: 595 (1970). If the coupling reaction was incomplete, repeat steps (10-16) or, alternatively, cap synthesis using N-acetyl imidazole (0.30M in DMF) or an excess of acetic anhydride in CH$_2$Cl$_2$.

Procedure B

Preparation of Boc-AA$_n$-p-Methylbenzhydrylamine resin

The selected Boc-AA$_n$-OH is attached to a p-Methylbenzhydrylamine (pMBHA) resin via N,N'-dicyclohexylcarbodiimide, as described below.

Schedule B
(1) Wash the pMBHA.HCl resin;
(2) Wash the resin 2× with 10% (V/V) DIPEA in CH$_2$Cl$_2$;
(3) Wash 2× with CH$_2$Cl$_2$;
(4) Wash 2× with MeOH;
(5) Wash 2× with CH$_2$Cl$_2$;
(6) Add 1-6 equivalents of preformed symmetrical anhydride of the suitably protected Boc-amino acid dissolved in CH$_2$Cl$_2$, with reaction time of 0.5-24 hrs.

Unreacted amino groups are acetylated with 0.30M N-acetylimidazole:DMF, or acetic anhydride:CH$_2$Cl$_2$. The following examples demonstrate the chemical synthesis of representative analog ANP compounds (identified as AP#) which illustrate certain aspects of the present invention.

EXAMPLE 1

*AP1

R-S-S-C-F-G-G-R-I-D-R-I-G-A-Q-S-G-C-N-S-F-R-Y

One gm of Boc-Y(2BrZ)-O-Resin (0.54 meq/gm, Peninsula Labs Inc., Belmont, CA) was subjected to procedure A with the required sequence of amino acids (introduced in order as Boc-R(Tos)-OH, Boc-F-OH, Boc-S(Bzl)-OH, Boc-N-OH, Boc-C(4-CH$_3$Bzl)-OH, Boc-G-OH, Boc-S(Bzl)-OH, Boc-Q-OH, Boc-A-OH, Boc-G-OH, Boc-I-OH.½H$_2$O, Boc-R(Tos)-OH, Boc-D(OBzl)-OH, Boc-I-OH.½H$_2$O, Boc-R(Tos)-OH, Boc-G-OH, Boc-G-OH, Boc-F-OH, Boc-C(4-CH3Bzl)-OH, Boc-S-(Bzl)-OH, Boc-S-(Bzl)-OH, Boc-R(Tos)-OH. The protected peptidyl resin was treated with TFA:CH$_2$Cl$_2$:EDT (45:50:5 v/v/v) for 1 min., then 20 min. and washed 3 times with CH$_2$Cl$_2$ and 2 times with MeOH to give the TFA salt of the peptidyl resin, and dried in vacuo.

The peptidyl resin was then suspended in anhydrous hydrogen fluoride (HF) containing 10% anisole, 2% ethyl methyl sulfide for 30 min. at −10° C., and 30 min. at 0° C. The HF was removed by evaporation under vacuum and the peptide/resin mixture was suspended in diethyl ether. The peptide/resin mixture was washed twice with diethyl ether, once with chloroform, once with diethyl ether, once with chloroform and once with diethyl ether. The peptide was extracted from the mixture with 2.0M acetic acid, diluted with H$_2$O and lyophilized, to give the unoxidized sulfhydryl peptide.

The crude peptide was dissolved in deoxygenated 0.01M ammonium acetate (NH$_4$OAc), pH 7.9, to 0.5 mg/ml and then oxidized by dropwise addition of a slight excess of 0.01M potassium ferricyanide (KCN) solution, stirred for 20 minutes and adjusted to pH 5 with acetic acid. The peptide solution was treated with DOWEX AG3X4 anion exchange resin, filtered, diluted with H$_2$O and lyophilized to give the crude cyclized peptide.

Purification of the peptide was achieved by desalting on Sephadex ® G-25F (Pharmacia Fine Chemicals) using 0.5M AcOH as eluant, followed by ion exchange chromatography on CM-Sepharose ® (Pharmacia Fine Chemicals) or CM-cellulose (Whatman) using an elution gradient generated by addition of 300 mM NH$_4$OAc, pH 6.5, to a solution of 10 mM NH$_4$OAc, pH 4.5. Fractions were collected having a minimum 97% purity, as judged by reversed phase HPLC, then pooled and lyophilized from H$_2$O several times to yield the purified AP1 acetate salt.

EXAMPLE 2

*AP2

R-S-S-C-G-R-I-D-R-I-G-A-Q-S-G-C-N-S-F-R-Y 1 gm of Boc-Y(2BrZ)-O-Resin (0.54 meq/gm, Peninsula Labs Inc., Belmont, CA) was subjected to procedure A with the required sequence of amino acids (introduced in order as Boc-R(Tos)-OH, Boc-F-OH, Boc-S(Bzl)-OH, Boc-N-OH, Boc-C(4-CH$_3$Bzl)-OH, Boc-G-OH, Boc-S(Bzl)-OH, Boc-Q-OH, Boc-A-OH, Boc-G-OH, Boc-I-OH.½H$_2$O, Boc-R(Tos)-OH, Boc-D(OBzl)-OH, Boc-I-OH.½H$_2$O, Boc-R(Tos)-OH, Boc-G-OH, Boc-C(4CH$_3$Bzl)-OH, Boc-S(Bzl)-OH, Boc-S(Bzl)-OH, Boc-R(Tos)-OH. The protected peptidyl resin was treated with TFA:CH$_2$Cl$_2$:EDT (45:50:5 v/v/v) for 1 min., then 20 min. and washed 3 times with CH$_2$Cl$_2$, 2 times with MeOH and dried in vacuo to give the TFA salt of the peptidyl resin.

The peptidyl resin was then suspended in anhydrous HF containing 10% anisole, 2% ethyl methyl sulfide for 30 min. at −10° C. and for 30 min. at 0° C. The HF was removed by evaporation under vacuum and the peptide/resin mixture was suspended in diethyl ether. The peptide/resin mixture was washed twice with diethyl ether, twice with chloroform, and twice with diethyl ether. The peptide was extracted with 2.0M acetic acid and lyophilized, to give the unoxidized sulfhydryl peptide.

The crude peptide was dissolved in deoxygenated 0.01M NH$_4$OAc, pH 7.9, to 0.5 mg/ml and then oxidized by dropwise addition of a slight excess of 0.01M KCN solution, stirred for 20 minutes and adjusted to pH 5 with acetic acid. The peptide solution was treated with DOWEX AG3X4 anion exchange resin, filtered, diluted with H₂O and lyophilized to give the crude cyclized peptide.

Purification of the peptide was achieved by desalting on Sephadex® G-25F using 0.5M AcOH as eluant, followed by ion exchange chromatography on CM-Sepharose® or CM-cellulose (Whatman) using an elution gradient generated by addition of 300 mM NH₄OAc, pH 6.5, to a solution of 10 mM NH₄OAc, pH 4.5. Fractions were collected having a minimum 97% purity, as judged by reversed phase HPLC, then pooled and lyophilized from H₂O several times to yield the purified AP2 acetate salt.

EXAMPLE 3

*AP3
R-S-S-C-F-G-G-R-I-D-R-I-G-A-Q-S-C-N-S-F-R-Y

One gm of Boc-Y(2BrZ)-O-Resin (0.54 meq/gm, Peninsula Labs Inc., Belmont, CA) was subjected to procedure A with the required sequence of amino acids (introduced in order as Boc-R(Tos)-OH, Boc-F-OH, Boc-S(Bzl)-OH, Boc-N-OH, Boc-C(4-CH₃Bzl)-OH, Boc-S(Bzl)-OH, Boc-Q-OH, Boc-A-OH, Boc-G-OH, Boc-I-OH.½H₂O, Boc-R(Tos)-OH, Boc-D(OBzl)-OH, Boc-I-OH.½H₂O, Boc-R(Tos)-OH, Boc-G-OH, Boc-G-OH, Boc-F-OH, Boc-C(4CH₃Bzl)-OH, Boc-S(Bzl)-OH, Boc-S(Bzl)-OH, Boc-R(Tos)-OH). The protected peptidyl resin was treated with TFA:CH₂Cl₂:EDT (45:50:5 v/v/v) for 1 min., then 20 min. and washed 3 times with CH₂Cl₂ and twice with MeOH to give the TFA salt of the peptidyl resin and dried in vacuo.

The peptidyl resin was then suspended in anhydrous HF containing 10% anisole, 2% ethyl methyl sulfide for 30 min. at −10° C. and for 30 min. at 0° C. The HF was removed by evaporation under vacuum and the peptide/resin mixture was suspended in diethyl ether. The peptide/resin mixture was washed twice with diethyl ether, once with chloroform, once with diethyl ether, once with chloroform and once again with diethyl ether. The peptide was extracted from the mixture with 2.0M acetic acid, diluted with H₂O and lyophilized, to give the unoxidized sulfhydryl peptide.

The crude peptide was dissolved in deoxygenated 0.01M NH₄OAc, pH 8, to 0.5 mg/ml and then oxidized by dropwise addition of a slight excess of 0.01M KCN solution, stirred 20 minutes and adjusted to pH 5 with acetic acid. The peptide solution was treated with DOWEX AG3X4 anion exchange resin, filtered, diluted with H₂O and lyophilized to give the crude cyclized peptide.

Purification of the peptide was achieved by desalting on Sephadex® G-25F using 0.5M AcOH as eluant, followed by ion exchange chromatography on CM-Sepharose® or CM-cellulose (Whatman) using an elution gradient generated by addition of 300 mM NH₄OAc to a solution of 10 mM NH₄OAc, pH 4.5. Fractions were collected having a minimum 97% purity, as judged by reversed phase HPLC, then pooled and lyophilized from H₂O several times to yield the purified AP3 acetate salt.

EXAMPLE 4

*AP4 R-S-S-C-F-G-G-R-I-D-R-I-G-A-C-N-S-F-NH₂

One gm of Boc-F-pMBHA resin, obtained using schedule B, was subjected to procedure A with the required sequence of amino acids (introduced in order as Boc-S(Bzl)-OH, Boc-N-OH, Boc-C(4-CH₃Bzl)-OH, Boc-A-OH, Boc-G-OH, Boc-I-OH.½H₂O, Boc-R(Tos)-OH, Boc-D(OBzl)-OH, Boc-I-OH.½H₂O, Boc-R(Tos)-OH, Boc-G-OH, Boc-G-OH, Boc-F-OH, Boc-C(4-CH₃Bzl)-OH, Boc-S(Bzl)-OH, Boc-S(Bzl)-OH, Boc-R(Tos)-OH). The peptidyl resin was then suspended in anhydrous HF containing 10% anisole, 2% ethyl methyl sulfide for 30 min. at −10° C. and for 30 min. at 0° C. The HF was removed by evaporation under vacuum and the peptide/resin mixture was suspended in diethyl ether. The peptide/resin mixture was washed twice with diethyl ether, once with chloroform, once with diethyl ether, once with chloroform and once again with diethyl ether. The peptide was extracted from the mixture with 2.0M acetic acid, diluted with H₂O and lyophilized, to give the unoxidized sulfhydryl peptide.

The crude peptide was dissolved in deoxygenated 0.01M NH₄OAc, pH 8, to 0.5 mg/ml and then oxidized by dropwise addition of a slight excess of 0.01M KCN, stirred for 20 minutes and adjusted to pH 5 with acetic acid. The peptide solution was treated with DOWEX AG3X4 anion exchange resin, filtered, diluted with H₂O and lyophilized to give the crude cyclized peptide.

Purification of the peptide was achieved by desalting on Sephadex® G-25F using 0.5M AcOH as eluant, followed by ion exchange chromatography on CM-Sepharose® or CM-cellulose (Whatman) using an elution gradient generated by addition of 300 mM NH₄OAc to a solution of 10 mM NH₄OAc, pH 4.5. Fractions were collected having a minimum 97% purity, as judged by reversed phase HPLC, then pooled and lyophilized from H₂O several times to yield the purified AP4 acetate salt.

Following the procedures outlined in Examples 1–4 (to produce analog peptides AP1–4) with appropriate modification, the following ANP analogs are synthesized (without showing any disulfide bonds):

| | |
|---|---|
| AP5 | S—L—R—R—S—S—C—F—G—G—R—I—D—R—I—G—A—Q—S—G—C—N—S—F—R—Y |
| AP6 | S—L—R—R—S—S—C—F—G—G—R—I—D—R—I—G—A—C—N—S—F—R—Y |
| AP7 | S—L—R—R—S—S—C—F—G—G—R—I—D—R—I—G—C—N—S—F—NH₂ |
| *AP8 | S—L—R—R—S—S—C—G—R—I—D—R—I—G—A—Q—S—G—L—G—C—N—S—F—R—Y |
| *AP9 | S—L—R—R—S—S—C—G—R—I—D—R—I—G—A—Q—S—G—L—G—C—N—S—F—NH₂ |
| AP10 | S—L—R—R—S—S—C—F—G—G—R—I—D—R—I—G—A—C—NH₂ |
| *AP11 | S—L—R—R—S—S—C—G—R—I—D—R—I—G—A—Q—S—G—L—G—C—NH₂ |
| AP12 | L—R—R—S—S—C—F—G—G—R—I—D—R—I—G—A—C—N—S—F—R |
| *AP13 | L—R—R—S—S—C—F—G—G—R—I—D—R—I—G—C—N—S—F—R—Y |
| *AP14 | R—R—S—S—C—F—G—G—R—I—D—R—I—G—A—Q—S—G—C—N—S—F—R—Y |
| AP15 | R—R—S—S—C—F—G—G—R—I—D—R—I—G—C—N—S—F—R—Y |

-continued

| | |
|---|---|
| AP16 | R—R—S—S—C—G—R—I—D—R—I—G—A—Q—S—G—L—G—C—N—S—F—R—Y |
| AP17 | R—R—S—S—C—F—G—G—R—I—D—R—I—G—A—Q—C—N—S—F—R—Y |
| *AP18 | R—S—S—C—F—G—G—R—I—D—R—I—G—A—Q—S—G—L—C—N—S—F—R—Y |
| *AP19 | R—S—S—C—F—G—G—R—I—D—R—I—G—A—Q—C—N—S—F—R—Y |
| *AP20 | R—S—S—C—F—G—G—R—I—D—R—I—G—A—C—N—S—F—R—Y |
| *AP21 | R—S—S—C—F—G—G—R—I—D—R—I—G—C—N—S—F—R—Y |
| *AP22 | R—S—S—C—F—G—G—R—I—D—R—I—C—N—S—F—R—Y |
| *AP23 | R—S—S—C—G—G—R—I—D—R—I—G—A—Q—S—G—L—G—C—N—S—F—R—Y |
| *AP24 | R—S—S—C—G—R—I—D—R—I—G—A—Q—S—G—L—G—C—N—S—F—R—Y |
| *AP25 | R—S—S—C—R—I—D—R—I—G—A—Q—S—G—L—G—C—N—S—F—R—Y |
| AP26 | S—S—C—F—G—G—R—I—D—R—I—G—A—C—N—S—F—NH$_2$ |
| AP27 | S—S—C—G—R—I—D—R—I—G—A—Q—S—G—L—G—C—N—S—F—R—Y |
| AP28 | S—S—C—R—I—D—R—I—G—A—Q—S—G—C—N—S—F—R—Y |
| AP29 | S—S—C—F—G—G—R—I—D—R—I—G—A—Q—C—N—S—F—R—Y |
| AP30 | S—C—F—G—G—R—I—D—R—I—G—A—C—N—S—F—R—Y |
| AP31 | S—C—G—R—I—D—R—I—G—A—Q—S—G—C—N—S—F—R—Y |
| AP32 | S—C—G—G—R—I—D—R—I—G—A—Q—S—G—C—N—S—F—NH$_2$ |
| AP33 | C—F—G—G—R—I—D—R—I—G—A—Q—S—G—C |
| AP34 | C—F—G—G—R—I—D—R—I—G—A—Q—S—C |
| AP35 | C—F—G—G—R—I—D—R—I—G—A—Q—C |
| *AP36 | C—F—G—G—R—I—D—R—I—G—A—C |
| *AP37 | C—F—G—G—R—I—D—R—I—G—A—C—NH$_2$ |
| *AP38 | C—F—G—G—R—M—D—R—I—G—A—C—NH$_2$ |
| AP39 | C—F—G—G—R—M—D—R—I—G—A—C |
| *AP40 | C—F—G—G—R—I—D—R—I—G—C |
| *AP41 | C—F—G—G—R—I—D—R—I—G—C—NH$_2$ |
| AP42 | C—F—G—G—R—I—D—R—I—C |
| *AP43 | C—F—G—G—R—M—D—R—I—C—NH$_2$ |
| AP44 | C—G—R—I—D—R—I—G—C |
| *AP45 | C—G—R—I—D—R—I—G—C—NH$_2$ |
| AP46 | C—G—R—M—D—R—I—G—C—NH$_2$ |
| *AP47 | C—R—I—D—R—I—G—A—C—NH$_2$ |
| AP48 | C—R—I—D—R—I—G—A—C |
| AP49 | C—R—I—D—R—I—G—C |
| *AP50 | C—R—I—D—R—I—G—C—NH$_2$ |
| AP51 | C—R—M—D—R—I—G—C |
| AP52 | C—R—I—D—R—I—C |
| AP53 | C—R—M—D—R—I—C—NH$_2$ |
| *AP54 | R—S—S—C—I—D—R—I—G—A—Q—S—G—L—G—C—N—S—F—R—Y |
| *AP55 | R—S—S—C—F—G—R—I—D—R—I—G—A—Q—S—G—L—G—C—N—S—F—R—Y |
| AP56 | L—R—R—S—S—C—F—G—G—R—I—D—R—I—G—C—N—S—F—R—Y |
| *AP57 | R—S—S—C—F—G—G—R—I—D—R—I—G—A—C—NH$_2$ |
| *AP58 | R—S—S—C—F—G—G—R—I—D—R—I—G—C—NH$_2$ |
| *AP59 | C—F—G—G—R—I—D—R—I—G—A—C—N—S—F—R—Y |
| *AP60 | C—R—I—D—R—I—G—A—Q—S—G—L—G—C—N—S—F—NH$_2$ |
| AP61 | S—S—C—F—G—G—R—I—D—R—I—G—A—C—N—S—F—NH$_2$ |
| *AP62 | C—F—G—G—R—I—D—R—I—G—A—C—N—S—F—NH$_2$ |
| *AP63 | R—C—F—G—G—R—I—D—R—I—G—A—C—N—S—F—NH$_2$ |
| *AP64 | C—R—I—D—R—I—G—A—Q—S—G—L—G—C—NH$_2$ |
| *AP65 | C—R—I—D—R—I—G—A—Q—S—G—L—C—NH$_2$ |
| *AP66 | C—F—G—G—R—I—D—R—I—G—A—Q—S—G—L—C—NH$_2$ |
| *AP67 | C—F—G—G—R—I—D—R—I—G—A—Q—S—G—C—NH$_2$ |
| *AP68 | C—F—G—G—R—I—D—R—I—G—A—Q—S—C—NH$_2$ |
| *AP69 | C—F—G—G—R—I—D—R—I—G—A—Q—C—NH$_2$ |
| *AP70 | Y—C—F—G—G—R—I—D—R—I—G—A—C—NH$_2$ |
| *AP71 | C—R—I—D—R—I—G—A—Q—S—G—C—NH$_2$ |
| *AP72 | C—G—G—R—M—D—R—I—G—A—C—NH$_2$ |
| *AP73 | C—G—R—I—D—R—I—G—A—C—NH$_2$ |
| *AP74 | C—F—G—R—I—D—R—I—G—A—C—NH$_2$ |
| *AP75 | C—F—R—I—D—R—I—G—A—C—NH$_2$ |
| *AP76 | R—C—F—G—G—R—I—D—R—I—G—A—C—NH$_2$ |
| *AP77 | C—G—G—R—I—D—R—I—G—C—NH$_2$ |
| *AP78 | C—R—I—D—R—I—G—A—Q—S—C—NH$_2$ |
| *AP79 | C—F—A—G—R—I—D—R—I—G—A—C—NH$_2$ |
| *AP80 | C—F—G—A—R—I—D—R—I—G—A—C—NH$_2$ |
| *AP81 | C—F—G—G—R—I—D—R—I—Aib—A—C—NH$_2$ |
| *AP82 | C—F—G—G—R—I—D—R—I—G—Aib—C—NH$_2$ |
| *AP83 | [D—C]—F—G—G—R—I—D—R—I—G—A—C—NH$_2$ |
| *AP84 | C—F—[D—A]—G—R—I—D—R—I—G—A—C—NH$_2$ |
| *AP85 | C—F—[D—S]—G—R—I—D—R—I—G—A—C—NH$_2$ |
| *AP86 | C—F—[D—L]—G—R—I—D—R—I—G—A—C—NH$_2$ |
| *AP87 | C—F—G—[D—A]—R—I—D—R—I—G—A—C—NH$_2$ |
| *AP88 | C—F—G—G—[D—R]—I—D—R—I—G—A—C—NH$_2$ |
| *AP89 | C—F—G—G—R—[D—I]—D—R—I—G—A—C—NH$_2$ |
| *AP90 | C—F—G—G—R—I—[D—D]—R—I—G—A—C—NH$_2$ |
| *AP91 | C—[D—F]—G—G—R—I—D—R—I—G—A—C—NH$_2$ |
| *AP92 | C—F—G—G—R—I—D—[D—R]—I—G—A—C—NH$_2$ |
| *AP93 | C—F—G—G—R—I—D—R—[D—I]—G—A—C—NH$_2$ |

-continued

| | |
|---|---|
| *AP94 | C—F—G—G—R—I—D—R—I—[D—A]—A—C—NH₂ |
| *AP95 | C—F—G—G—R—I—D—R—I—G—[D—A]—C—NH₂ |
| *AP96 | C—F—G—G—R—I—D—R—I—G—A—[D—C]—NH₂ |
| *AP97 | R—S—S—C—F—[D—A]—G—R—I—D—R—I—G—A—C—NH₂ |
| *AP98 | C—F—[D—A]—G—R—I—D—R—I—G—C—NH₂ |
| *AP99 | Acetyl-C—F—G—G—R—I—D—R—I—G—A—C—NH₂ |
| *AP100 | A—F—G—G—R—I—D—R—I—G—A—A—NH₂ |
| *AP101 | A—F—G—G—R—I—D—R—I—G—A—NH₂ |
| *AP102 | A—F—G—G—R—I—D—R—I—G—NH₂ |
| *AP103 | A—F—G—G—R—I—D—R—I—NH₂ |
| *AP104 | F—G—G—R—I—D—R—I—G—A—A—NH₂ |
| *AP105 | G—G—R—I—D—R—I—G—A—A—NH₂ |
| *AP106 | G—R—I—D—R—I—G—A—A—NH₂ |
| *AP107 | R—I—D—R—I—G—A—A—NH₂ |
| AP108 | C—F—G—G—R—I—D—R—I—G—A—C—N—S—F—R |
| *AP109 | R—C—F—G—G—R—I—D—R—I—G—A—C—N—S—F—NH₂ |
| *AP110 | C—F—G—G—R—I—D—R—I—G—C—N—S—F—NH₂ |
| *AP111 | C—F—[D—V]—G—R—I—D—R—I—G—A—C—NH₂ |
| *AP112 | C—F—Aib—G—R—I—D—R—I—G—A—C—NH₂ |
| *AP113 | C—F—G—G—R—[D—M]—D—R—I—G—A—C—NH₂ |
| *AP114 | C—A—G—G—R—I—D—R—I—G—A—C—NH₂ |
| AP115 | C—[D—A]—G—G—R—I—D—R—I—G—A—C—NH₂ |
| AP116 | C—F—G—G—R—I—D—R—[D—V]—G—A—C—NH₂ |
| AP117 | C—F—G—G—R—I—E—R—I—G—A—C—NH₂ |
| AP118 | A—F—G—G—R—M—D—R—I—G—NH₂ |
| *AP119 | F—G—G—R—I—D—R—I—NH₂ |
| *AP120 | Acetyl-G—G—R—I—D—R—I—NH₂ |
| AP121 | G—R—I—D—R—I—NH₂ |
| *AP122 | F—G—G—R—I—D—R—I—G—NH₂ |
| AP123 | G—G—R—I—D—R—I—G—NH₂ |
| AP124 | G—R—I—D—R—I—G—NH₂ |
| AP125 | R—I—D—R—I—G—NH₂ |
| *AP126 | F—G—G—R—I—D—R—I—G—A—NH₂ |
| AP127 | G—G—R—I—D—R—I—G—A—NH₂ |
| AP128 | G—R—I—D—R—I—G—A—NH₂ |
| AP129 | R—I—D—R—I—G—A—NH₂ |
| *AP130 | (desNH₂—F)—G—G—R—I—D—R—I—G—A—NH₂ |
| AP131 | (desNH₂—F)—G—G—R—I—D—R—I—G—NH₂ |
| *AP132 | (desNH₂—F)—G—G—R—I—D—R—I—NH₂ |
| *AP133 | A—F—[D—A]—G—R—I—D—R—I—G—A—NH₂ |
| AP134 | A—F—[D—A]—G—R—I—D—R—I—G—NH₂ |
| AP135 | A—F—[D—A]—G—R—I—D—R—I—NH₂ |
| AP136 | F—[D—A]—G—R—I—D—R—I—G—A—NH₂ |
| AP137 | F—[D—A]—G—R—I—D—R—I—G—NH₂ |
| AP138 | F—[D—A]—G—R—I—D—R—I—NH₂ |
| AP139 | (desNH₂—F)—[D—A]—G—R—I—D—R—I—G—A—NH₂ |
| AP140 | (desNH₂—F)—[D—A]—G—R—I—D—R—I—G—NH₂ |
| AP141 | (desNH₂—F)—[D—A]—G—R—I—D—R—I—NH₂ |
| AP142 | A—F—[D—S]—G—R—I—D—R—I—G—A—NH₂ |
| AP143 | A—F—[D—S]—G—R—I—D—R—I—G—NH₂ |
| AP144 | A—F—[D—S]—G—R—I—D—R—I—NH₂ |
| AP145 | F—[D—S]—G—R—I—D—R—I—G—A—NH₂ |
| AP146 | F—[D—S]—G—R—I—D—R—I—G—NH₂ |
| AP147 | F—[D—S]—G—R—I—D—R—I—NH₂ |
| AP148 | (desNH₂—F)—[D—S]—G—R—I—D—R—I—G—A—NH₂ |
| AP149 | (desNH₂—F)—[D—S]—G—R—I—D—R—I—G—NH₂ |
| AP150 | (desNH₂—F)—[D—S]—G—R—I—D—R—I—NH₂ |
| *AP151 | A—[D—F]—G—G—R—I—D—R—I—G—A—NH₂ |
| AP152 | A—[D—F]—G—G—R—I—D—R—I—G—NH₂ |
| AP153 | A—[D—F]—G—G—R—I—D—R—I—NH₂ |
| AP154 | [D—F]—G—G—R—I—D—R—I—G—A—NH₂ |
| AP155 | [D—F]—G—G—R—I—D—R—I—G—NH₂ |
| AP156 | [D—F]—G—G—R—I—D—R—I—NH₂ |
| AP157 | A—F—G—[D—A]—R—I—D—R—I—G—A—NH₂ |
| AP158 | A—F—G—[D—A]—R—I—D—R—I—G—NH₂ |
| AP159 | A—F—G—[D—A]—R—I—D—R—I—NH₂ |
| AP160 | F—G—[D—A]—R—I—D—R—I—G—A—NH₂ |
| AP161 | F—G—[D—A]—R—I—D—R—I—G—NH₂ |
| AP162 | F—G—[D—A]—R—I—D—R—I—NH₂ |
| AP163 | (desNH₂—F)—G—[D—A]—R—I—D—R—I—G—A—NH₂ |
| AP164 | (desNH₂—F)—G—[D—A]—R—I—D—R—I—G—NH₂ |
| AP165 | (desNH₂—F)—G—[D—A]—R—I—D—R—I—NH₂ |
| AP166 | A—F—G—G—R—I—D—R—I—[D—A]—NH₂ |
| AP167 | F—G—G—R—I—D—R—I—G—[D—A]—NH₂ |
| AP168 | (desNH₂—F)—G—G—R—I—D—R—I—G—[D—A]—NH₂ |
| AP169 | A—F—G—G—R—I—D—R—I—[D—A]—A—NH₂ |
| AP170 | F—G—G—R—I—D—R—I—[D—A]—A—NH₂ |
| AP171 | (desNH₂—F)—G—G—R—I—D—R—I—[D—A]—A—NH₂ |
| AP172 | A—F—G—G—R—I—D—R—I—[D—A]—NH₂ |
| AP173 | F—G—G—R—I—D—R—I—[D—A]—NH₂ |
| AP174 | (desNH₂—F)—G—G—R—I—D—R—I—[D—A]—NH₂ |
| AP175 | Y—A—F—G—G—R—I—D—R—I—G—A—NH₂ |

-continued

| | |
|---|---|
| AP176 | A—F—G—G—R—I—D—R—I—G—Y—NH$_2$ |
| AP177 | A—F—G—G—R—I—E—R—I—G—A—NH$_2$ |
| AP178 | A—F—G—G—K—I—E—R—I—G—A—NH$_2$ |
| AP179 | A—F—G—G—K—I—D—R—I—G—A—NH$_2$ |
| AP180 | A—F—G—G—R—I—D—K—I—G—A—NH$_2$ |
| AP181 | (desNH$_2$—F)—G—G—R—M—D—R—I—G—A—NH$_2$ |
| AP182 | (desNH$_2$—F)—G—G—R—M—D—R—I—G—NH$_2$ |
| AP183 | (desNH$_2$—F)—G—G—R—M—D—R—I—NH$_2$ |
| AP184 | A—F—[D—A]—G—R—M—D—R—I—G—A—NH$_2$ |
| AP185 | A—F—[D—A]—G—R—M—D—R—I—G—NH$_2$ |
| AP186 | A—F—[D—A]—G—R—M—D—R—I—NH$_2$ |
| AP187 | F—[D—A]—G—R—M—D—R—I—G—A—NH$_2$ |
| AP188 | F—[D—A]—G—R—M—D—R—I—G—NH$_2$ |
| AP189 | F—[D—A]—G—R—M—D—R—I—NH$_2$ |
| AP190 | (desNH$_2$—F)—[D—A]—G—R—M—D—R—I—G—A—NH$_2$ |
| AP191 | (desNH$_2$—F)—[D—A]—G—R—M—D—R—I—G—NH$_2$ |
| AP192 | (desNH$_2$—F)—[D—A]—G—R—M—D—R—I—NH$_2$ |
| AP193 | A—F—[D—S]—G—R—M—D—R—I—G—A—NH$_2$ |
| AP194 | A—F—[D—S]—G—R—M—D—R—I—G—NH$_2$ |
| AP195 | A—F—[D—S]—G—R—M—D—R—I—NH$_2$ |
| AP196 | F—[D—S]—G—R—M—D—R—I—G—A—NH$_2$ |
| AP197 | F—[D—S]—G—R—M—D—R—I—G—NH$_2$ |
| AP198 | F—[D—S]—G—R—M—D—R—I—NH$_2$ |
| AP199 | (desNH$_2$—F)—[D—S]—G—R—M—D—R—I—G—A—NH$_2$ |
| AP200 | (desNH$_2$—F)—[D—S]—G—R—M—D—R—I—G—NH$_2$ |
| AP201 | (desNH$_2$—F)—[D—S]—G—R—M—D—R—I—NH$_2$ |
| AP202 | A—[D—F]—G—G—R—M—D—R—I—G—A—NH$_2$ |
| AP203 | A—[D—F]—G—G—R—M—D—R—I—G—NH$_2$ |
| AP204 | A—[D—F]—G—G—R—M—D—R—I—NH$_2$ |
| AP205 | [D—F]—G—G—R—M—D—R—I—G—A—NH$_2$ |
| AP206 | [D—F]—G—G—R—M—D—R—I—G—NH$_2$ |
| AP207 | [D—F]—G—G—R—M—D—R—I—NH$_2$ |
| AP208 | A—F—G—[D—A]—R—M—D—R—I—G—A—NH$_2$ |
| AP209 | A—F—G—[D—A]—R—M—D—R—I—G—NH$_2$ |
| AP210 | A—F—G—[D—A]—R—M—D—R—I—NH$_2$ |
| AP211 | F—G—[D—A]—R—M—D—R—I—G—A—NH$_2$ |
| AP212 | F—G—[D—A]—R—M—D—R—I—G—NH$_2$ |
| AP213 | F—G—[D—A]—R—M—D—R—I—NH$_2$ |
| AP214 | (desNH$_2$—F)—G—[D—A]—R—M—D—R—I—G—A—NH$_2$ |
| AP215 | (desNH$_2$—F)—G—[D—A]—R—M—D—R—I—G—NH$_2$ |
| AP216 | (desNH$_2$—F)—G—[D—A]—R—M—D—R—I—NH$_2$ |
| AP217 | A—F—G—G—R—M—D—R—I—G—[D—A]—NH$_2$ |
| AP218 | F—G—G—R—M—D—R—I—G—[D—A]—NH$_2$ |
| AP219 | (desNH$_2$—F)—G—G—R—M—D—R—I—G—[D—A]—NH$_2$ |
| AP220 | A—F—G—G—R—M—D—R—I—[D—A]—A—NH$_2$ |
| AP221 | F—G—G—R—M—D—R—I—[D—A]—A—NH$_2$ |
| AP222 | (desNH$_2$—F)—G—G—R—M—D—R—I—[D—A]—A—NH$_2$ |
| AP223 | A—F—G—G—R—M—D—R—I—[D—A]—NH$_2$ |
| AP224 | F—G—G—R—M—D—R—I—[D—A]—NH$_2$ |
| AP225 | (desNH$_2$—F)—G—G—R—M—D—R—I—[D—A]—NH$_2$ |
| AP226 | Y—A—F—G—G—R—M—D—R—I—G—A—NH$_2$ |
| AP227 | A—F—G—G—R—M—D—R—I—G—Y—NH$_2$ |
| AP228 | A—F—G—G—R—M—E—R—I—G—A—NH$_2$ |
| AP229 | A—F—G—G—K—M—E—R—I—G—A—NH$_2$ |
| AP230 | A—F—G—G—K—M—D—R—I—G—A—NH$_2$ |
| AP231 | A—F—G—G—R—M—D—K—I—G—A—NH$_2$ |
| AP232 | R—S—S—C—F—G—G—R—M—D—R—I—G—A—C—NH$_2$ |
| AP233 | R—S—S—C—F—G—G—R—M—D—R—I—G—C—NH$_2$ |
| AP234 | C—F—G—G—R—M—D—R—I—G—A—C—N—S—F—R—Y |
| AP235 | C—R—M—D—R—I—G—A—Q—S—G—L—G—C—N—S—F—NH$_2$ |
| AP236 | S—S—C—F—G—G—R—M—D—R—I—G—A—C—N—S—F—NH$_2$ |
| AP237 | C—F—G—G—R—M—D—R—I—G—A—C—N—S—F—NH$_2$ |
| AP238 | R—C—F—G—G—R—M—D—R—I—G—A—C—N—S—F—NH$_2$ |
| AP239 | C—R—M—D—R—I—G—A—Q—S—G—L—G—C—NH$_2$ |
| AP240 | C—R—M—D—R—I—G—A—Q—S—G—L—C—NH$_2$ |
| AP241 | C—F—G—G—R—M—D—R—I—G—A—Q—S—G—L—C—NH$_2$ |
| AP242 | C—F—G—G—R—M—D—R—I—G—A—Q—S—G—C—NH$_2$ |
| AP243 | C—F—G—G—R—M—D—R—I—G—A—Q—S—C—NH$_2$ |
| AP244 | C—F—G—G—R—M—D—R—I—G—A—Q—C—NH$_2$ |
| AP245 | Y—C—F—G—G—R—M—D—R—I—G—A—C—NH$_2$ |
| AP246 | C—R—M—D—R—I—G—A—Q—S—G—C—NH$_2$ |
| AP247 | C—G—R—M—D—R—I—G—A—C—NH$_2$ |
| *AP248 | C—F—G—R—M—D—R—I—G—A—C—NH$_2$ |
| AP249 | C—F—R—M—D—R—I—G—A—C—NH$_2$ |
| AP250 | R—C—F—G—G—R—M—D—R—I—G—A—C—NH$_2$ |
| AP251 | C—G—G—R—M—D—R—I—G—C—NH$_2$ |
| AP252 | C—R—M—D—R—I—G—A—Q—S—C—NH$_2$ |
| AP253 | C—F—A—G—R—M—D—R—I—G—A—C—NH$_2$ |
| AP254 | C—F—G—A—R—M—D—R—I—G—A—C—NH$_2$ |
| AP255 | C—F—G—G—R—M—D—R—I—Aib—A—C—NH$_2$ |
| AP256 | C—F—G—G—R—M—D—R—I—G—Aib—C—NH$_2$ |
| AP257 | [D—C]—F—G—G—R—M—D—R—I—G—A—C—NH$_2$ |

-continued

| | |
|---|---|
| AP258 | C—F—[D—A]—G—R—M—D—R—I—G—A—C—NH₂ |
| AP259 | C—F—[D—S]—G—R—M—D—R—I—G—A—C—NH₂ |
| AP260 | C—F—[D—L]—G—R—M—D—R—I—G—A—C—NH₂ |
| AP261 | C—F—G—[D—A]—R—M—D—R—I—G—A—C—NH₂ |
| AP262 | C—F—G—G—[D—R]—M—D—R—I—G—A—C—NH₂ |
| AP263 | C—F—G—G—R—[D—M]—D—R—I—G—A—C—NH₂ |
| AP264 | C—F—G—G—R—M—[D—D]—R—I—G—A—C—NH₂ |
| AP265 | C—[D—F]—G—G—R—M—D—R—I—G—A—C—NH₂ |
| AP266 | C—F—G—G—R—M—D—[D—R]—I—G—A—C—NH₂ |
| AP267 | C—F—G—G—R—M—D—R—[D—I]—G—A—C—NH₂ |
| AP268 | C—F—G—G—R—M—D—R—I—[D—A]—A—C—NH₂ |
| AP269 | C—F—G—G—R—M—D—R—I—G—[D—A]—C—NH₂ |
| AP270 | C—F—G—G—R—M—D—R—I—G—A—[D—C]—NH₂ |
| AP271 | R—S—S—C—F—[D—A]—G—R—M—D—R—I—G—A—C—NH₂ |
| AP272 | C—F—[D—A]—G—R—M—D—R—I—G—C—NH₂ |
| AP273 | Acetyl-C—F—G—G—R—M—D—R—I—G—A—C—NH₂ |
| AP274 | A—F—G—G—R—M—D—R—I—G—A—A—NH₂ |
| AP275 | A—F—G—G—R—M—D—R—I—G—A—NH₂ |
| AP276 | A—F—G—G—R—M—D—R—I—NH₂ |
| AP277 | F—G—G—R—M—D—R—I—G—A—A—NH₂ |
| AP278 | G—G—R—M—D—R—I—G—A—A—NH₂ |
| AP279 | G—R—M—D—R—I—G—A—A—NH₂ |
| AP280 | R—M—D—R—I—G—A—A—NH₂ |
| AP281 | C—F—G—G—R—M—D—R—I—G—A—C—N—S—F—NH₂ |
| AP282 | R—C—F—G—G—R—M—D—R—I—G—A—C—N—S—F—NH₂ |
| AP283 | C—F—G—G—R—M—D—R—I—G—C—N—S—F—NH₂ |
| AP284 | C—F—[D—V]—G—R—M—D—R—I—G—A—C—NH₂ |
| AP285 | C—F—Aib—G—R—M—D—R—I—G—A—C—NH₂ |
| AP286 | C—A—G—G—R—M—D—R—I—G—A—C—NH₂ |
| AP287 | C—[D—A]—G—G—R—M—D—R—I—G—A—C—NH₂ |
| AP288 | C—F—G—G—R—M—D—R—[D—V]—G—A—C—NH₂ |
| AP289 | C—F—G—G—R—M—E—R—I—G—A—C—NH₂ |
| AP290 | F—G—G—R—M—D—R—I—NH₂ |
| AP291 | Acetyl-G—G—R—M—D—R—I—NH₂ |
| AP292 | G—R—M—D—R—I—NH₂ |
| AP293 | F—G—G—R—M—D—R—I—G—NH₂ |
| AP294 | G—G—R—M—D—R—I—G—NH₂ |
| AP295 | G—R—M—D—R—I—G—NH₂ |
| AP296 | R—M—D—R—I—G—NH₂ |
| AP297 | F—G—G—R—M—D—R—I—G—A—NH₂ |
| AP298 | G—G—R—M—D—R—I—G—A—NH₂ |
| AP299 | G—R—M—D—R—I—G—A—NH₂ |
| AP300 | R—M—D—R—I—G—A—NH₂ |
| *AP301 | A—F—G—G—[D—R]—I—D—R—I—G—A—NH₂ |
| *AP302 | A—F—G—G—R—[D—I]—D—R—I—G—A—NH₂ |
| *AP303 | A—F—G—G—R—I—[D—D]—R—I—G—A—NH₂ |
| *AP304 | A—F—G—G—R—I—D—[D—R]—I—G—A—NH₂ |
| *AP305 | A—F—G—G—R—I—D—R—[D—I]—G—A—NH₂ |

In each of the above examples, designated "*", amino acid analysis demonstrated that the appropriate amino acid sequence of the peptide was obtained.

The following examples demonstrate the chemical synthesis of representative organic substituent group modified analog peptide compounds (identified as AP#) which illustrate certain aspects of the present invention.

EXAMPLE 306

*AP306 [2-Napthylacetyl]-G-G-R-I-D-R-I-G-A-NH₂

One gm of Boc-A-pMBHA resin (0.4 meq/gm), obtained using schedule B, was subjected to procedure A with the required sequence of amino acids and Aminoterminal substituent group (introduced in order as Boc-G-OH, Boc-I-OH.½H₂O, Boc-R(Tos)-OH, Boc-D(OBzl)-OH, Boc-I-OH.½H₂O, Boc-R(Tos)-OH, Boc-G-OH, Boc-G-OH, 2-Napthylacetic acid). The protected peptidyl resin was washed 3 times with CH₂Cl₂ and 3 times with MeOH and dried in vacuo.

The peptidyl resin was then suspended in anhydrous HF containing 10% anisole, 2% ethyl methyl sulfide for 30 min. at −10° C. and for 30 min. at 0° C. The HF was removed by evaporation under vacuum and the peptide/resin mixture was suspended in ethyl ether. After transfer to a fritted funnel, the peptide/resin mixture was washed twice with ethyl ether, once with chloroform, once with ethyl ether, once with chloroform and once again with ethyl ether. The peptide was then extracted from the mixture with 2.0M acetic acid, diluted with H₂O and lyophilized.

Purification of the peptide was achieved by ion exchange chromatography on CM-Sepharose ® (Pharmacia) using an elution gradient generated by addition of 100 mM NH₄OAc, pH 6.5, to a solution of 10 mM NH₄OAc, pH 4.5. Fractions were monitored at 254 nm and analyzed by reversed phase HPLC. Fractions having a minimum 97% purity were pooled and lyophilized from H₂O several times to yield the purified AP306 acetate salt.

EXAMPLE 307

*AP307

[2-Napthoxyacetyl]-NH(CH₂)₄C(=O)—R—I—D-R—I—NH₂

One gm of Boc-I-pMBHA resin (0.4 meq/gm), obtained using schedule B, was subjected to procedure A with the required sequence of amino acids and Aminoterminal substituent group (introduced in order as Boc- R(Tos)-OH, Boc-D(OBzl)-OH, Boc-I-OH.½H₂O, Boc-R(Tos)-OH, Boc-NH(CH₂)₄COOH, 2-Napthoxyacetic acid). The protected peptidyl resin was washed three times with CH₂Cl₂ and three times with MeOH and dried in vacuo.

The peptidyl resin was then suspended in anhydrous HF containing 10% anisole, 2% ethyl methyl sulfide for 30 min. at −10° C. and for 30 min. at 0° C. The HF was removed by evaporation under vacuum and the peptide/resin mixture was suspended in ethyl ether. After transfer to a fritted funnel, the peptide/resin mixture was washed twice with ethyl ether, once with chloroform, once with ethyl ether, once with chloroform and once again with ethyl ether. The peptide was then extracted from the mixture with 2.0M acetic acid, diluted with H₂O and lyophilized.

Purification of the peptide was achieved by ion exchange chromatography on CM-Sepharose ® (Pharmacia) using an elution gradient generated by addition of 100 mM NH₄OAc, pH 6.5, to a solution of 10 mM NH₄OAc, pH 4.5. Fractions were monitored at 254 nm and analyzed by reversed phase HPLC. Fractions having a minimum 97% purity were pooled and lyophilized from H₂O several times to yield the purified AP307 acetate salt.

Following the procedures outlined in Examples 306 and 307 (to produce analog peptides AP306 and AP307) with appropriate modification, the following ANP analogs were synthesized:

*AP308 [Triphenylpropionyl]-G—G—R—I—D—R—I—NH₂
*AP309 [1-Adamantylacetyl]-G—G—R—I—D—R—I—NH₂
*AP310 [CBZ]-G—G—R—I—D—R—I—NH₂
*AP311 [FMOC]-G—G—R—I—D—R—I—NH₂
*AP312 [FMOC]-G—G—R—I—D—R—I—G—A—NH₂
*AP313 [Indolepropionyl]-G—G—R—I—D—R—I—G—A—NH₂
*AP314 [2-Napthylacetyl]-G—G—R—I—D—R—I—NH₂
*AP315 [1-Napthylacetyl]-G—G—R—I—D—R—I—G—A—NH₂
*AP316 [1-Napthoxyacetyl]-G—G—R—I—D—R—I—NH₂
*AP317 [4-Biphenylacetyl]-G—G—R—I—D—R—I—NH₂
*AP318 [2-Napthoxyacetyl]-G—G—R—I—D—R—I—G—A—NH₂
*AP319 [2-Napthoxyacetyl]-G—G—R—I—D—R—I—NH₂
*AP320 [2-Napthylacetyl]-G—[Sar]-R—I—D—R—I—NH₂
*AP321 [2-Napthylacetyl]-G—[Aib]-R—I—D—R—I—NH₂
*AP322 [2-Napthoxyacetyl]-[D—A]-G—R—I—D—R—I—NH₂

*AP323 [FMOC]-NH(CH₂)₄C(=O)—R—I—D—R—I—NH₂
*AP324 [2-Napthylacetyl]-NH(CH₂)₄C(=O)—R—I—D—R—I—NH₂

*AP325 [2-Napthoxyacetyl]-NH(CH₂)₅C(=O)—R—I—D—R—I—NH₂

*AP326 [FMOC]-NH(CH₂)₃C(=O)—R—I—D—R—I—NH₂
*AP327 [2-Napthylacetyl]-NH(CH₂)₃C(=O)—R—I—D—R—I—NH₂

*AP328 [2-Napthylacetyl]-G—G—R—I—D—R—I—NHCH₂CH₃

*AP329 [2-Napthylacetyl]-NH(CH₂)₅C(=O)—R—I—D—R—I—NH₂
*AP330 [2-Napthylacetyl]-[D—S]-G—R—I—D—R—I—NH₂

*AP331 [Diphenylpropionyl]-G—G—R—I—D—R—I—G—A—NH₂
*AP332 [2-Napthylacetyl]-G—G—R—I—D—R—L—NH₂
*AP333 [2-Napthylacetyl]-G—G—R—I—D—R—V—NH₂
*AP334 [Cyclohexylacetyl]-G—G—R—I—D—R—I—NH₂
AP335 [2-Napthoxyacetyl]-G—G—R—M—D—Q—I—G—A—NH₂
AP336 [2-Napthoxyacetyl]-G—G—R—M—D—Q—I—G—NH₂
*AP337 [2-Napthoxyacetyl]-G—G—R—M—D—Q—I—NH₂
AP338 [2-Napthoxyacetyl]-G—G—A—I—D—R—I—NH₂
AP339 [2-Napthoxyacetyl]-G—G—A—I—D—R—I—G—NH₂
AP340 [2-Napthoxyacetyl]-G—G—A—I—D—R—I—G—A—NH₂
AP341 [2-Napthoxyacetyl]-G—G—A—M—D—R—I—G—A—NH₂
AP342 [2-Napthoxyacetyl]-G—G—A—M—D—R—I—G—NH₂
AP343 [2-Napthoxyacetyl]-G—G—A—M—D—R—I—NH₂
AP344 [2-Napthylacetyl]-G—G—R—M—D—R—V—NH₂
AP345 [2-Napthylacetyl]-G—G—R—M—D—R—L—NH₂
AP346 [2-Napthylacetyl]-G—G—R—M—D—R—M—NH₂
AP347 [2-Napthylacetyl]-G—G—R—V—D—R—I—NH₂
AP348 [2-Napthylacetyl]-G—G—R—M—D—R—V—NH₂
AP349 [2-Napthylacetyl]-G—G—R—V—D—R—L—NH₂
AP350 [2-Napthylacetyl]-G—G—R—M—D—R—M—NH₂
*AP351 [2-Napthylacetyl]-G—G—R—I—D—Q—I—NH₂
AP352 [2-Napthylacetyl]-G—G—R—I—D—Q—I—G—NH₂
AP353 [2-Napthylacetyl]-G—G—R—I—D—Q—I—G—A—NH₂
AP354 [2-Napthylacetyl]-G—G—R—M—D—Q—I—G—A—NH₂
AP355 [2-Napthylacetyl]-G—G—R—M—D—Q—I—G—NH₂
AP356 [2-Napthylacetyl]-G—G—R—M—D—Q—I—NH₂
*AP357 [2-Napthylacetyl]-G—G—A—I—D—R—I—NH₂
AP358 [2-Napthylacetyl]-G—G—A—I—D—R—I—G—NH₂
AP359 [2-Napthylacetyl]-G—G—A—I—D—R—I—G—A—NH₂
AP360 [2-Napthylacetyl]-G—G—A—M—D—R—I—G—A—NH₂
AP361 [2-Napthylacetyl]-G—G—A—M—D—R—I—G—NH₂
AP362 [2-Napthylacetyl]-G—G—A—M—D—R—I—NH₂
AP363 [2-Napthoxyacetyl]-G—G—R—I—D—R—V—NH₂
AP364 [2-Napthoxyacetyl]-G—G—R—M—D—R—V—NH₂
*AP365 [2-Napthoxyacetyl]-G—G—R—I—D—R—L—NH₂
AP366 [2-Napthoxyacetyl]-G—G—R—I—D—R—M—NH₂
AP367 [2-Napthoxyacetyl]-G—G—R—M—D—R—M—NH₂
AP368 [2-Napthoxyacetyl]-G—G—R—M—D—R—L—NH₂
AP369 [2-Napthoxyacetyl]-G—G—R—I—D—Q—I—NH₂
AP370 [2-Napthoxyacetyl]-G—G—R—I—D—Q—I—G—NH₂
AP371 [2-Napthoxyacetyl]-G—G—R—I—D—Q—I—G—A—NH₂
AP372 [2-Napthoxyacetyl]-G—G—R—I—D—R—I—G—NH₂
AP373 [2-Napthoxyacetyl]-G—G—R—M—D—R—I—NH₂
AP374 [2-Napthoxyacetyl]-G—[Aib]-R—I—D—R—I—NH₂
AP375 [2-Napthoxyacetyl]-G—[Aib]-R—I—D—R—I—G—NH₂
AP376 [2-Napthoxyacetyl]-G—[Aib]-R—I—D—R—I—G—A—NH₂
AP377 [2-Napthoxyacetyl]-G—[Aib]-R—M—D—R—I—G—A—NH₂
AP378 [2-Napthoxyacetyl]-G—[Aib]-R—M—D—R—I—G—NH₂

```
AP379 [2-Napthoxyacetyl]-G—[Aib]-R—M—D—R—I—NH2
AP380 [2-Napthoxyacetyl]-G—[Sar]-R—I—D—R—I—G—NH2
AP381 [2-Napthoxyacetyl]-G—[Sar]-R—I—D—R—I—NH2
AP382 [2-Napthoxyacetyl]-G—[Sar]-R—I—D—R—I—G—A—NH2
AP383 [2-Napthoxyacetyl]-G—[Sar]-R—M—D—R—I—G—A—NH2
AP384 [2-Napthoxyacetyl]-G—[Sar]-R—M—D—R—I—G—NH2
AP385 [2-Napthoxyacetyl]-G—[Sar]-R—M—D—R—I—NH2      AP386 [2-Napthylacetyl]-G—[Sar]-R—I—D—R—I—G—NH2
AP387 [2-Napthylacetyl]-G—[Sar]-R—I—D—R—I—G—A—NH2
AP388 [2-Napthylacetyl]-G—[Sar]-R—M—D—R—I—G—A—NH2
AP389 [2-Napthylacetyl]-G—[Sar]-R—M—D—R—I—G—NH2
*AP390 [2-Napthylacetyl]-G—[Sar]-R—M—D—R—I—NH2
AP391 [2-Napthoxyacetyl]-G—G—R—I—D—R—I—NHCH2CH3
AP392 [2-Napthoxyacetyl]-G—G—R—I—D—R—I—NH2        AP393 [2-Napthoxyacetyl]-G—G—R—I—D—R—I—G—NH2
AP394 [2-Napthoxyacetyl]-G—G—R—M—D—R—I—G—A—NH2
AP395 [2-Napthoxyacetyl]-G—G—R—M—D—R—I—G—NH2
AP396 [2-Napthoxyacetyl]-G—G—R—M—D—R—I—NH2
AP397 [2-Napthoxyacetyl]-[D—S]-G—R—M—D—R—I—G—NH2
AP398 [2-Napthoxyacetyl]-[D—S]-G—R—M—D—R—I—NH2
AP399 [2-Napthoxyacetyl]-G—[D—A]-R—I—D—R—I—NH2
AP400 [2-Napthoxyacetyl]-G—[D—A]-R—I—D—R—I—G—NH2
AP401 [2-Napthoxyacetyl]-G—[D—A]-R—M—D—R—I—G—A—NH2
AP402 [2-Napthoxyacetyl]-G—[D—A]-R—M—D—R—I—G—NH2
AP403 [2-Napthoxyacetyl]-G—[D—A]-R—M—F—R—I—NH2
*AP404 [2-Napthylacetyl]-G—[D—A]-R—I—D—R—I—NH2
AP405 [2-Napthylacetyl]-G—[D—A]-R—I—D—R—I—G—NH2
AP406 [2-Napthylacetyl]-G—[D—A]-R—I—D—R—I—G—A—NH2
AP407 [2-Napthylacetyl]-G—[D—A]-R—M—D—R—I—G—A—NH2
AP408 [2-Napthylacetyl]-G—[D—A]-R—M—D—R—I—G—NH2
AP409 [2-Napthylacetyl]-G—[D—A]-R—M—D—R—I—NH2
AP410 [2-Napthylacetyl]-G—[Aib]-R—I—D—R—I—G—NH2
AP411 [2-Napthylacetyl]-G—[Aib]-R—I—D—R—I—G—A—NH2
AP412 [2-Napthylacetyl]-G—[Aib]-R—M—D—R—I—G—A—NH2
AP413 [2-Napthylacetyl]-G—[Aib]-R—M—D—R—I—G—NH2
*AP414 [2-Napthylacetyl]-G—[Aib]-R—M—D—R—I—NH2
```

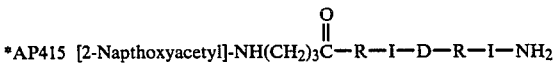

*AP415 [2-Napthoxyacetyl]-NH(CH2)3C(=O)—R—I—D—R—I—NH2

AP416 [2-Napthoxyacetyl]-NH(CH2)3C(=O)—R—I—D—R—I—G—NH2

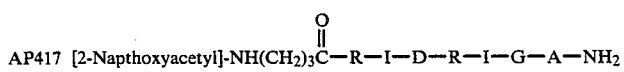

AP417 [2-Napthoxyacetyl]-NH(CH2)3C(=O)—R—I—D—R—I—G—A—NH2

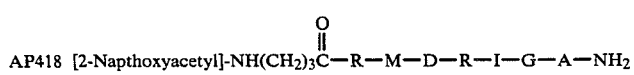

AP418 [2-Napthoxyacetyl]-NH(CH2)3C(=O)—R—M—D—R—I—G—A—NH2

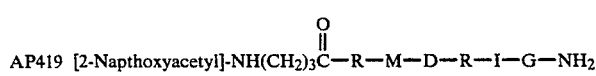

AP419 [2-Napthoxyacetyl]-NH(CH2)3C(=O)—R—M—D—R—I—G—NH2

AP420 [2-Napthoxyacetyl]-NH(CH2)3C(=O)—R—M—D—R—I—NH2

AP421 [2-Napthoxyacetyl]-NH(CH2)5C(=O)—R—I—D—R—I—G—NH2

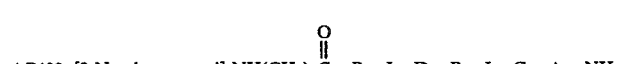

AP422 [2-Napthoxyacetyl]-NH(CH2)5C(=O)—R—I—D—R—I—G—A—NH2

AP423 [2-Napthoxyacetyl]-NH(CH2)5C(=O)—R—M—D—R—I—G—A—NH2

AP424 [2-Napthoxyacetyl]-NH(CH2)5C(=O)—R—M—D—R—I—G—NH2

AP425 [2-Napthoxyacetyl]-NH(CH2)5C(=O)—R—M—D—R—I—NH2

AP426 [2-Napthylacetyl]-NH(CH2)5C(=O)—R—M—D—R—I—NH2

AP427 [2-Napthylacetyl]-NH(CH$_2$)$_5$C(=O)—R—M—D—R—I—G—NH$_2$

AP428 [2-Napthylacetyl]-NH(CH$_2$)$_5$C(=O)—R—M—D—R—I—G—A—NH$_2$

*AP429 [2-Napthylacetyl]-NH(CH$_2$)$_5$C(=O)—R—I—D—R—I—G—A—NH$_2$

AP430 [2-Napthylacetyl]-NH(CH$_2$)$_5$C(=O)—R—I—D—R—I—G—NH$_2$

AP431 [2-Napthylacetyl]-[D—S]-G—R—I—D—R—I—G—NH$_2$
AP432 [2-Napthylacetyl]-[D—S]-G—R—I—D—R—I—G—A—NH$_2$
AP433 [2-Napthylacetyl]-[D—S]-G—R—M—D—R—I—G—A—NH$_2$
AP434 [2-Napthylacetyl]-[D—S]-G—R—M—D—R—I—G—NH$_2$
AP435 [2-Napthylacetyl]-[D—S]-G—R—M—D—R—I—NH$_2$
AP436 [2-Napthoxyacetyl]-[D—S]-G—R—I—D—R—I—NH$_2$
AP437 [2-Napthoxyacetyl]-[D—S]-G—R—I—D—R—I—G—NH$_2$
AP438 [2-Napthoxyacetyl]-[D—S]-G—R—I—D—R—I—G—A—NH$_2$
AP439 [2-Napthylacetyl]-[D—S]-G—R—M—D—R—I—G—A—NH$_2$
*AP440 [2-Napthylacetyl]-[D—A]-G—R—I—D—R—I—NH$_2$
AP441 [2-Napthylacetyl]-[D—A]-G—R—I—D—R—I—G—NH$_2$
AP442 [2-Napthylacetyl]-[D—A]-G—R—I—D—R—I—G—A—NH$_2$
AP443 [2-Napthylacetyl]-[D—A]-G—R—M—D—R—I—G—A—NH$_2$
AP444 [2-Napthylacetyl]-[D—A]-G—R—M—D—R—I—G—NH$_2$
AP445 [2-Napthylacetyl]-[D—A]-G—R—M—D—R—I—NH$_2$
AP446 [2-Napthoxyacetyl]-[D—A]-G—R—I—D—R—I—G—NH$_2$
AP447 [2-Napthoxyacetyl]-[D—A]-G—R—I—D—R—I—G—A—NH$_2$
AP448 [2-Napthoxyacetyl]-[D—A]-G—R—M—D—R—I—G—A—NH$_2$
AP449 [2-Napthoxyacetyl]-[D—A]-G—R—M—D—R—I—G—NH$_2$
AP450 [2-Napthoxyacetyl]-[D—A]-G—R—M—D—R—I—NH$_2$ AP451 [2-Napthylacetyl]-NH(CH$_2$)$_3$C(=O)—R—I—D—R—I—G—NH$_2$ AP452 [2-Napthylacetyl]-NH(CH$_2$)$_3$C(=O)—R—I—D—R—I—G—A—NH$_2$ AP453 [2-Napthylacetyl]-NH(CH$_2$)$_3$C(=O)—R—M—D—R—I—G—A—NH$_2$ AP454 [2-Napthylacetyl]-NH(CH$_2$)$_3$C(=O)—R—M—D—R—I—G—NH$_2$ AP455 [2-Napthylacetyl]-NH(CH$_2$)$_3$C(=O)—R—M—D—R—I—NH$_2$ AP456 [2-Napthoxyacetyl]-NH(CH$_2$)$_4$C(=O)—R—I—D—R—I—G—NH$_2$ AP457 [2-Napthoxyacetyl]-NH(CH$_2$)$_4$C(=O)—R—I—D—R—I—G—A—NH$_2$ AP458 [2-Napthoxyacetyl]-NH(CH$_2$)$_4$C(=O)—R—M—D—R—I—G—NH$_2$

*AP459 [2-Napthoxyacetyl]-NH(CH$_2$)$_4$C(=O)—R—M—D—R—I—NH$_2$

AP460 [2-Napthoxyacetyl]-NH(CH$_2$)$_4$C(=O)—R—I—D—R—V—NH$_2$

AP461 [2-Napthoxyacetyl]-NH(CH$_2$)$_4$C(=O)—R—I—D—R—L—NH$_2$

AP462 [2-Napthoxyacetyl]-NH(CH$_2$)$_4$C(=O)—R—I—D—R—M—NH$_2$

-continued

AP463 [2-Napthoxyacetyl]-NH(CH$_2$)$_4$C(=O)—R—M—D—R—M—NH$_2$

AP464 [2-Napthoxyacetyl]-NH(CH$_2$)$_4$C(=O)—R—M—D—R—V—NH$_2$

AP465 [2-Napthoxyacetyl]-NH(CH$_2$)$_4$C(=O)—R—M—D—R—L—NH$_2$

AP466 [2-Napthoxyacetyl]-NH(CH$_2$)$_4$C(=O)—R—L—D—R—L—NH$_2$

AP467 [2-Napthoxyacetyl]-NH(CH$_2$)$_4$C(=O)—R—L—D—R—M—NH$_2$

AP468 [2-Napthoxyacetyl]-NH(CH$_2$)$_4$C(=O)—R—L—D—R—V—NH$_2$

AP469 [2-Napthoxyacetyl]-NH(CH$_2$)$_4$C(=O)—R—L—D—R—I—NH$_2$

AP470 [2-Napthoxyacetyl]-NH(CH$_2$)$_4$C(=O)—R—V—D—R—I—NH$_2$

AP471 [2-Napthoxyacetyl]-NH(CH$_2$)$_4$C(=O)—R—V—D—R—V—NH$_2$

AP472 [2-Napthoxyacetyl]-NH(CH$_2$)$_4$C(=O)—R—V—D—R—L—NH$_2$

AP473 [2-Napthoxyacetyl]-NH(CH$_2$)$_4$C(=O)—R—V—D—R—M—NH$_2$

AP474 [2-Napthoxyacetyl]-NH(CH$_2$)$_4$C(=O)—A—I—D—R—I—NH$_2$

AP475 [2-Napthoxyacetyl]-NH(CH$_2$)$_4$C(=O)—A—M—D—R—I—NH$_2$

AP476 [2-Napthoxyacetyl]-NH(CH$_2$)$_4$C(=O)—R—I—D—Q—I—NH$_2$

AP477 [2-Napthoxyacetyl]-NH(CH$_2$)$_4$C(=O)—R—I—D—Q—I—G—NH$_2$

AP478 [2-Napthoxyacetyl]-NH(CH$_2$)$_4$C(=O)—R—I—D—Q—I—G—A—NH$_2$

AP479 [2-Napthoxyacetyl]-NH(CH$_2$)$_4$C(=O)—R—M—D—Q—I—G—A—NH$_2$

AP480 [2-Napthoxyacetyl]-NH(CH$_2$)$_4$C(=O)—R—M—D—Q—I—G—NH$_2$

AP481 [2-Napthoxyacetyl]-NH(CH$_2$)$_4$C(=O)—R—M—D—Q—I—NH$_2$

AP482 [2-Napthyacetyl]-NH(CH$_2$)$_4$C(=O)—R—I—D—R—I—G—NH$_2$

*AP483 [2-Napthyacetyl]-NH(CH$_2$)$_4$C(=O)—R—I—D—R—I—G—A—NH$_2$

AP484 [2-Napthyacetyl]-NH(CH$_2$)$_4$C(=O)—R—M—D—R—I—G—A—NH$_2$

AP485 [2-Napthyacetyl]-NH(CH$_2$)$_4$C(=O)—R—M—D—R—I—G—NH$_2$

*AP486 [2-Napthyacetyl]-NH(CH$_2$)$_4$C(=O)—R—M—D—R—I—NH$_2$

AP487 [2-Napthyacetyl]-NH(CH$_2$)$_4$C(=O)—R—I—D—R—V—NH$_2$

*AP488 [2-Napthyacetyl]-NH(CH$_2$)$_4$C(=O)—R—I—D—R—L—NH$_2$

AP489 [2-Napthyacetyl]-NH(CH$_2$)$_4$C(=O)—R—I—D—R—M—NH$_2$

AP490 [2-Napthyacetyl]-NH(CH$_2$)$_4$C(=O)—R—M—D—R—M—NH$_2$

AP491 [2-Napthyacetyl]-NH(CH$_2$)$_4$C(=O)—R—M—D—R—L—NH$_2$

AP492 [2-Napthyacetyl]-NH(CH$_2$)$_4$C(=O)—R—M—D—R—V—NH$_2$

AP493 [2-Napthyacetyl]-NH(CH$_2$)$_4$C(=O)—A—I—D—R—I—NH$_2$

AP494 [2-Napthyacetyl]-NH(CH$_2$)$_4$C(=O)—A—M—D—R—I—NH$_2$

AP495 [2-Napthyacetyl]-NH(CH$_2$)$_4$C(=O)—R—I—D—Q—I—NH$_2$

AP496 [2-Napthyacetyl]-NH(CH$_2$)$_4$C(=O)—R—M—D—Q—I—NH$_2$

AP497 [2-Napthyacetyl]-NH(CH$_2$)$_4$C(=O)—R—I—D—Q—I—G—NH$_2$

AP498 [2-Napthyacetyl]-NH(CH$_2$)$_4$C(=O)—R—I—D—Q—I—G—A—NH$_2$

AP499 [2-Napthyacetyl]-NH(CH$_2$)$_4$C(=O)—R—M—D—Q—I—G—A—NH$_2$

AP500 [2-Napthyacetyl]-NH(CH$_2$)$_4$C(=O)—R—M—D—Q—I—G—NH$_2$

*AP501 [2-Napthylacetyl]-NH(CH$_2$)$_4$C(=O)—R—L—D—R—I—NH$_2$

AP502 [2-Napthylacetyl]-NH(CH$_2$)$_4$C(=O)—R—L—D—R—M—NH$_2$

AP503 [2-Napthylacetyl]-NH(CH$_2$)$_4$C(=O)—R—L—D—R—V—NH$_2$

AP504 [2-Napthylacetyl]-NH(CH$_2$)$_4$C(=O)—R—L—D—R—L—NH$_2$

AP505 [2-Napthylacetyl]-NH(CH$_2$)$_4$C(=O)—R—V—D—R—I—NH$_2$

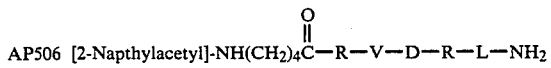
AP506 [2-Napthylacetyl]-NH(CH₂)₄C(=O)—R—V—D—R—L—NH₂

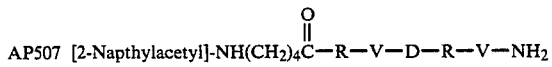
AP507 [2-Napthylacetyl]-NH(CH₂)₄C(=O)—R—V—D—R—V—NH₂

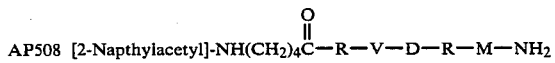
AP508 [2-Napthylacetyl]-NH(CH₂)₄C(=O)—R—V—D—R—M—NH₂

In each of the above examples designated "*", amino acid analysis demonstrated that the appropriate amino acid sequence of the peptide was obtained.

II. Biological Testing

Biological activity data for selected analog Atrial Natriuretic Peptides (ANPs) which were synthesized as disclosed above are presented below as biochemical, isolated tissue and whole mammal bioassays.

Without intending to be bound by any theory, it is believed that the activity of the ANP analog compounds of the invention is due to their affinity for receptors in the kidney and other sites which are responsible for influencing the clearance of the endogenous ANPs. The following in vitro biological data show that the analog compounds of the invention compete with an iodinated native ANP molecule for binding to receptors from cultured bovine aortic smooth muscle (BASM) cells, and bovine endothelial (BAE) cells. This competition is, evidently, diagnostic for the binding to the relevant clearance receptors. This correlation is confirmed by in vitro data which demonstrate that analogs active in the competitive binding assay (subsection A) are able to cause diuresis and natriuresis in anesthetized rats and dogs and to lower blood pressure in anesthetized rats (subsection B). However, the analogs do not cause diuresis or natriuresis in isolated kidney, but potentiate the effect of "natural" ANP in the isolated tissue (subsection C). In addition, the analogs of the invention, either linear or reduced-member cyclic, show reduced cyclic GMP activity, an activity which is a hallmark of the direct biological function of ANP.

Thus, the results below demonstrate that a wide range of peptides within the scope of the invention test positive in an in vitro assay, which is then confirmed, using representative peptides, as a model for natriuretic/diuretic and vasodilator activity in vivo.

A. Receptor binding assays

Specific ANP receptors sites have been identified on target tissues, such as kidney, adrenal, blood vessels, and cultured cells. Napier, M. A., et al., Proc. Nat. Acad. Sci. USA 81: 5946–5940 (1984); DeLean, A., et al. Endocrinology 115: 1636–1638 (1984); Schenk, D. B., et al., Biochem. Biophys. Res. Comm. 127: 433–442 (1985). Since the binding of ANP or ANP analogs to these specific receptor sites is presumptively a prerequisite of biological activity, binding of ANP analogs to these receptors is considered predictive of biological activity.

An assay has been developed, generally in accordance with the disclosure of Schenk, supra, and Scarborough, R. M. et al., J. Biol. Chem. 261: 12960–12964 (1986), which evaluates the ability of ANP analogs to compete with a labeled native ANP for binding to cultured BASM and BAE cells. This native ANP, having the amino acid sequences:

R-S-S-C-F-G-G-R-I-D-R-I-G-A-Q-S-G-L-G-C-N-S-F-R-Y was iodinated on the Carboxy-terminal Y residue and is identified as [$^{125}$I]-rANP(126–150). Analogous "competitive displacement" receptor binding assays are considered commonplace in the art for examining specific ligand-receptor interactions. An example of the results of this ANP-receptor binding assay is presented in FIG. 1.

In this assay, 0.5 nM [$^{125}$I]-rANP(126–150) was incubated in each individual sample of BASM cells in the presence of varying amounts of unlabeled rANP(1-26-150) or a compound of the present invention having the amino acid sequence:

| AP25 | R—S—S—C—R—I—D—R—I—G—A—Q—S—G—L—G—C—N—S—F—R—Y |
| AP37 | C—F—G—G—R—I—D—R—I—G—A—C—NH₂ |
| AP101 | A—F—G—G—R—I—D—R—I—G—A—NH₂ or |
| AP132 | (desNH₂—F)—G—G—R—I—D—R—I—NH₂ |

As shown in FIG. 1, increasing concentrations of rANP(126–150), or analog peptides AP25, AP37, AP101 or AP132 effectively prevent [$^{125}$I]-rANP(1-26-150) binding to BASM cell-associated receptors. The concentration of unlabeled peptide at which 50% of maximal [$^{125}$I]-rANP(126–150) binding is displaced is called Ki(app) and reflects receptor-binding affinity. Therefore, hypothetical peptide A, with a Ki(app)=100 nM, displays substantially weaker interaction with a receptor than hypothetical peptide B with a Ki(app)=10 nM. Assuming these ANP analogs act at one or more ANP receptor sites, then increased receptor affinity should reflect increased biological potency.

Table IA, IB, IC, ID and IE present data which compare the concentrations at which analog compounds of the present invention displace [$^{125}$I]-rANP(126–150) binding from specific receptor sites on BASM or BAE cells. As will be shown below, these data correlate with in vivo activity characteristic of native ANP.

TABLE IA

| Peptide | Sequence | Ki(app) (nM) |
|---|---|---|
| rANP(126-150) | R—S—S—C—F—G—G—R—I—D—R—I—G— | 7.26 |

TABLE IA-continued

| Peptide | Sequence | Ki(app) (nM) |
|---|---|---|
| AP23 | R—S—S—C—G—G—R—I—D—R—I—G—<br>A—Q—S—G—L—G—C—N—S—F—R—Y | 7.76 |
| AP24 | R—S—S—C—G—R—I—D—R—I—G—<br>A—Q—S—G—L—G—C—N—S—F—R—Y | 25.2 |
| AP25 | R—S—S—C—R—I—D—R—I—G—<br>A—Q—S—G—L—G—C—N—S—F—R—Y | 8.62 |
| AP54 | R—S—S—C—I—D—R—I—G—<br>A—Q—S—G—L—G—C—N—S—F—R—Y | >100 |

Table IA compares receptor binding affinity (Ki(app)) of rANP(126-150) with Ki(app) of analog peptides wherein, for compounds of the invention AP23-25, the pentapeptide core is RIDRI and $Z_1$ and $Z_2$ are $X_1$-C-$X_2$ and $X_3$-C-$X_4$, respectively; $X_1$ is R-S-S, $X_3$ is G-A-Q-S-G-L-G, $X_4$ is N-S-F-R-Y and $X_2$ has been selected from the group consisting of G-G, G and des$X_2$. Also included, as a negative control, is AP54 which lacks a residue of the requisite pentapeptide.

Although analog peptide AP24, where $X_2$ is G, has a weaker apparent affinity, analog peptide AP23, where $X_2$ is G-G and analog peptide AP25, where $X_2$ is des$X_2$, exhibit equivalent receptor affinites to that of rANP(126-150). However, receptor binding capacity is substantially diminished for AP54. Thus AP54 should exhibit weaker biological activity if the Ki(app) correlates to activity.

The data in Table IA demonstrate that compounds of the invention are effective in receptor binding, as compared to the control compound, AP54. As is confirmed in Section B, below, compounds of the invention shown in Table IA exhibit in vivo activity whereas the negative control, AP54, does not.

TABLE IB

| Peptide | Sequence | Ki(app) (nM) |
|---|---|---|
| rANP(126-150) | R—S—S—C—F—G—G—R—I—D—R—I—G—<br>A—Q—S—G—L—G—C—N—S—F—R—Y | 7.26 |
| AP1 | R—S—S—C—F—G—G—R—I—D—R—I—G—<br>A—Q—S—G—C—N—S—F—R—Y | 6.88 |
| AP3 | R—S—S—C—F—G—G—R—I—D—R—I—G—<br>A—Q—S—C—N—S—F—R—Y | 9.12 |
| AP4 | R—S—S—C—F—G—G—R—I—D—R—I—G—<br>A—C—N—S—F—NH$_2$ | 1.41 |
| AP17 | R—S—S—C—F—G—G—R—I—D—R—I—G—<br>A—Q—C—N—S—F—R—Y | 7.35 |
| AP20 | R—S—S—C—F—G—G—R—I—D—R—I—G—<br>A—C—N—S—F—R—Y | 7.50 |
| AP21 | R—S—S—C—F—G—G—R—I—D—R—I—G—<br>C—N—S—F—R—Y | 15.15 |
| AP22 | R—S—S—C—F—G—G—R—I—D—R—I—<br>C—N—S—F—R—Y | >40 |

Table IB presents data which compares the Ki(app) of rANP(126-150) with analog peptides similar to those of Table IA, but wherein $X_1$ is R-S-S, $X_2$ is F-G-G, $X_4$ is N-S-F-R-Y or N-S-F-NH$_2$ and $X_3$ is selected from the group consisting of G-A-Q-S-G, G-A-Q-S, G-A-Q, G-A, G and dex$X_3$. These analogs show a high degree of receptor-binding affinity, although the affinity of AP22 was reduced.

TABLE IC

| Peptide | Sequence | Ki(app) (nM) |
|---|---|---|
| rANP(126-150) | R—S—S—C—F—G—G—R—I—D—R—I—G—<br>A—Q—S—G—L—G—C—N—S—F—R—Y | 7.26 |
| AP20 | R—S—S—C—F—G—G—R—I—D—R—I—G—<br>A—C—N—S—F—R—Y | 7.50 |
| AP36 | C—F—G—G—R—I—D—R—I—G—A—C | 14.92 |
| AP37 | C—F—G—G—R—I—D—R—I—G—A—C—NH$_2$ | 13.40 |
| AP62 | C—F—G—G—R—I—D—R—I—G—A—C—<br>N—S—F—NH$_2$ | 5.96 |
| AP109 | R—C—F—G—G—R—I—D—R—I—G—A—C—<br>N—S—F—NH$_2$ | 4.97 |
| AP110 | C—F—G—G—R—I—D—R—I—G—C—N—S—<br>F—NH$_2$ | 6.51 |
| AP64 | C—R—I—D—R—I—G—A—Q—S—G—L—G—<br>C—NH$_2$ | 12.39 |
| AP67 | C—F—G—G—R—I—D—R—I—G—A—Q—S—<br>G—C—NH$_2$ | 7.08 |
| AP69 | C—F—G—G—R—I—D—R—I—G—A—Q<br>C—NH$_2$ | 2.45 |
| AP65 | C—R—I—D—R—I—G—A—Q—S—<br>G—L—C—NH$_2$ | 14.04 |
| AP70 | Y—C—F—G—G—R—I—D—R—I—G—A—<br>C—NH$_2$ | 7.07 |
| AP83 | [D—C——F—G—G—R—I—D—R—I—G—A—<br>C—NH$_2$ | 5.75 |
| AP91 | C—[D—F]—G—G—R—I—D—R—I—G— | 24.03 |

TABLE IC-continued

| Peptide | Sequence | Ki(app) (nM) |
|---|---|---|
| AP84 | C—F—[D—A]—G—R—I—D—R—I—G—A—C—NH$_2$ | 13.29 |
| AP85 | C—F—[D—S]—G—R—I—D—R—I—G—A—C—NH$_2$ | 5.25 |
| AP86 | C—F—[D—L]—G—R—I—D—R—I—G—A—C—NH$_2$ | 14.04 |
| AP111 | C—F—[D—V]—G—R—I—D—R—I—G—A—C—NH$_2$ | 10.68 |
| AP112 | C—F—Aib—G—R—I—D—R—I—G—A—C—NH$_2$ | 69.57 |
| AP82 | C—F—G—G—R—I—D—R—I—G—Aib—C—NH$_2$ | 4.43 |
| AP113 | C—F—G—G—R—[D—M]—D—R—I—G—A—C—NH$_2$ | 15.77 |
| AP89 | C—F—G—G—R—[D—I]—D—R—I—G—A—C—NH$_2$ | >100 |
| AP90 | C—F—G—G—R—I—[D—D]—R—I—G—A—C—NH$_2$ | >100 |
| AP92 | C—F—G—G—R—I—D—[D—R]—I—G—A—C—NH$_2$ | >100 |
| AP94 | C—F—G—G—R—I—D—R—I—[D—A]—A—C—NH$_2$ | 26.73 |
| AP95 | C—F—G—G—R—I—D—R—I—G—A—[D—A]—C—NH$_2$ | 20.34 |
| AP96 | C—F—G—G—R—I—D—R—I—G—A—[D—C]—NH$_2$ | 3.75 |
| AP114 | C—A—G—G—R—I—D—R—I—G—A—C—NH$_2$ | >100 |
| AP115 | C—[D—A]—G—G—R—I—D—R—I—G—A—C—NH$_2$ | 18.27 |

Table IC shows additional data for compounds wherein the pentapeptide core R(I/M)DRI is retained, although with substitutions made in accordance with the preferences expressed previously. Table IC also provides additional embodiments of compounds wherein $Z_1$ is $X_1$-C-$X_2$ and $Z_2$ is $X_3$-C-$X_4$, including one compound (AP96) wherein one of the C residues is in the D form. Many of these compounds exhibit significant receptor binding activity. However, the diminished binding affinity of less preferred embodiment AP114 is currently under investigation, In addition, in some instances wherein the R(I/M)DRI pentapeptide core is altered, affinity is also greatly diminished.

Limitations on alterations of this core are shown in the series AP113, AP89, AP90 and AP92. Substitution of the D optical isomer for the L amino acid appears to diminish activity in all instances except in the case of D-M as AA9 in AP113. The remaining compounds with various embodiments of $Z_1$ and $Z_2$ bind to the receptors with high affinity.

Attention is called, in particular, to the demonstration, for example, for AP36, that both $X_1$ and $X_4$ may represent "peptides" with zero amino acid residues, and for AP112 and AP36, for example, $X_2$ and $X_3$ together may represent as few as 5 amino acids.

TABLE ID

| Peptide | Sequence | Ki(app) |
|---|---|---|
| rANP (126-150) | R—S—S—C—F—G—G—R—I—D-R—I—G—A—S—Q—G—L-G—C—N—S—F—R—Y | 7.50 |
| AP104 | F—G—G—R—I—D-R—I—G—A—A—NH$_2$ | 2.50 |
| AP101 | A—F—G—G—R—I—D-R—I—G—A—NH$_2$ | 2.63 |
| AP102 | A—F—G—G—R—I—D-R—I—G—NH$_2$ | 14.04 |
| AP103 | A—F—G—G—R—I—D-R—I—NH$_2$ | 12.42 |
| AP132 | (desNH$_2$—F)—G—G—R—I—D-R—I—NH$_2$ | 10.15 |
| AP125 | R—I—D-R—I—G—NH$_2$ | >100 |
| AP105 | G—G—R—I—D-R—I—G—A—A—NH$_2$ | >100 |
| AP175 | Y—A—F—G—G—R—I—D-R—I—G—A—NH$_2$ | 5.94 |
| AP126 | F—G—G—R—I—D-R—I—G—A—NH$_2$ | 2.16 |
| AP119 | F—G—G—R—I—D-R—I—NH$_2$ | 8.9 |
| AP176 | A—F—G—G—R—I—D-R—I—G—Y—NH$_2$ | 6.65 |
| AP151 | A—[D-F]—G—G—R—I—D-R—I—G—A—NH$_2$ | 39.6 |
| AP133 | A—F—[D-A]—G—R—I—D-R—I—G—A—NH$_2$ | 2.93 |
| AP157 | A—F—G—[D-A]—R—I—D-R—I—G—A—NH$_2$ | 5.90 |
| AP130 | (desNH$_2$—F)—G—G—R—I—D-R—I—G—A—NH$_2$ | 8.8 |
| AP301 | A—F—G—G—[D-R]—I—D-R—I—G—A—NH$_2$ | >100 |
| AP302 | A—F—G—G—R—[D-I]—D-R—I—G—A—NH$_2$ | 18.9 |
| AP303 | A—F—G—G—R—I—[D-D]—R—I—G—A—NH$_2$ | >100 |
| AP304 | A—F—G—G—R—I—D-[D-R]—I—G—A—NH$_2$ | 95.6 |
| AP305 | A—F—G—G—R—I—D-R—[D-I]—G—A—NH$_2$ | 70.62 |
| AP306 | [2-Napthylacetyl]-G—G—R—I—D-R—I—G—A—NH$_2$ | 2.03 |
| AP307 | [2-Napthoxyacetyl]-NH(CH$_2$)$_4$C(=O)—R—I—D-R—I—NH$_2$ | 39.9 |

TABLE ID-continued

| Peptide | Sequence | Ki(app) |
|---|---|---|
| AP309 | [1-Adamantylacetyl]-G—G—R—I—D-R—I—NH$_2$ | 30.0 |
| AP311 | [FMOC]—G—G—R—I—D-R—I—NH$_2$ | 10.33 |
| AP312 | [FMOC]—G—G—R—I—D-R—I—G—A—NH$_2$ | 6.27 |
| AP313 | [Indolepropionyl]-G—G—R—I—D-R—I—G—A—NH$_2$ | 4.52 |
| AP314 | [2-Napthylacetyl]-G—G—R—I—D-R—I—NH$_2$ | 14.5 |
| AP316 | [1-Napthoxyacetyl]-G—G—R—I—D-R—I—NH$_2$ | 50.4 |
| AP317 | [4-Biphenylacetyl]-G—G—R—I—D-R—I—NH$_2$ | 123.8 |
| AP318 | [2-Napthoxyacetyl]-G—G—R—I—D-R—I—G—A—NH$_2$ | 8.7 |
| AP319 | [2-Napthoxyacetyl]-G—G—R—I—D-R—I—NH$_2$ | 6.0 |
| AP320 | [2-Naphthylacetyl]-G—[Sar]-R—I—D-R—I—NH$_2$ | 47.4 |
| AP321 | [2-Naphthylacetyl]-G—[Aib]-R—I—D-R—I—NH$_2$ | 33.0 |
| AP322 | [2-Napthoxyacetyl]-[D-A]—G—R—I—D-R—I—NH$_2$ | >100 |
| AP323 | [FMOC]—NH(CH$_2$)$_4$C(=O)—R—I—D-R—I—NH$_2$ | 162.6 |
| AP324 | [2-Naphthylacetyl]-NH(CH$_2$)$_4$C(=O)—R—I—D-R—I—NH$_2$ | 48.5 |
| AP325 | [2-Napthoxyacetyl]-NH(CH$_2$)$_5$C(=O)—R—I—D-R—I—NH$_2$ | >100 |
| AP327 | [2-Naphthylacetyl]-NH(CH$_2$)$_3$C(=O)—R—I—D-R—I—NH$_2$ | 184 |
| AP328 | [2-Naphthylacetyl]-G—G—R—I—D-R—I—NHCH$_2$CH$_3$ | 19.87 |
| AP329 | [2-Naphthylacetyl]-NH(CH$_2$)$_5$C(=O)—R—I—D-R—I—NH$_2$ | 147.78 |
| AP330 | [2-Naphthylacetyl]-[D-S]—G—R—I—D-R—I—NH$_2$ | 16.4 |
| AP331 | [Diphenylpropionyl]-G—G—R—I—D-R—I—G—A—NH$_2$ | 6.15 |
| AP332 | [2-Naphthylacetyl]-G—G—R—I—D-R—L—NH$_2$ | 44.2 |
| AP333 | [2-Naphthylacetyl]-G—G—R—I—D-R—V—NH$_2$ | 106.4 |
| AP334 | [Cyclohexylacetyl]-G—G—R—I—D-R—I—NH$_2$ | 92.8 |
| AP338 | [2-Naphthylacetyl]-G—G—A—I—D-R—I—NH$_2$ | 82.6 |
| AP351 | [2-Napthylacetyl]-G—G—R—I—D-Q—I—NH$_2$ | 20.0 |

The data in Table ID represent the receptor binding activity of linear forms of the compounds of the invention wherein $Z_1$ is $Y_1-Y_2$ and $Z_2$ is NH$_2$, NHR', or a peptide of 1–20 amino acid residues, or an amide or alkyl amide thereof.

All of the compounds of Table ID fall within the scope of the inventon, except for AP125 and AP105, which lack the requisite hydrophobicity of $Y_1$; and AP301, AP303 and AP304, which do not contain pentapeptide cores included within the scope of the invention. These compounds appear to be inactive. The only other compounds with greatly diminished activity are AP317, AP322, AP323, AP325, AP329, and AP333. Of particular interest are the short peptide compounds A306, AP314, AP319 and AP324, which show high binding affinity and, as demonstrated below, display significant biological activity.

In order to show that the receptor binding assay is specific for ANP, Table IE provides data which compares ANP-receptor interactions of rANP(126-150) with the unrelated peptide hormones angiotensin II, glucagon, parathyroid hormone and γ-MSH.

TABLE IE

| Peptide | Ki(app) |
|---|---|
| rANP(126–150) | 7.50 |
| angiotensin II | >500 |
| glucagon | >500 |
| parathyroid hormone | >500 |
| γ-MSH | >500 |

As shown in TAble IE, only rANP(126–150) displays detectable ANP-receptor affinity. This attests to the relevant ANP-specificity of this receptor.

The data in the foregoing tables show that a large representative sample of the compounds of the invention demonstrate affinity in the specific receptor binding assay described. The following subsections demonstrate that representative compound of this class, which demonstrate receptor binding, are also active in vivo, whereas compounds which do not bind to these receptors appear inactive.

B. Whole mammal bioassays

The biological activity of analog compounds of the present invention can be demonstrated in anesthetized rats and dogs. The correlation of receptor binding affinity and in vivo effects demonstrates the predictive value of the receptor assays for biological activity.

1. Diuresis in anesthetized rats

In one set of examples, cannulae were placed in the left and right ureters and femoral vein of anesthetized rats and urine was collected from the ureters. Analog peptides were administered via the femoral vein. Prior to infusing the analog peptides, saline was infused for 30 minutes, urine was collected for 6 five minute baseline periods and urine volume was determined gravimetrically.

Following these baseline collection periods, various analog peptides were infused for 30 or 60 minutes and urine volume was measured in five minute periods during infusion and for 60 minutes following infusion (at which time rats were returned to saline). Data was examined by averaging urine flow rates for six five-minute baseline control periods immediately preceding infusion, and comparing values during and after administration of peptides with the "baseline" control values. Responses to peptides are thus evaluated and plotted as the percent of baseline control responses. Specific examples are shown in FIGS. 2A-H. The error bars at the beinning of the graphs represent baseline values ± standard deviations. Responses to peptides that are substantially above baseline ± SD can thus be interpreted as being statistically significant increases.

As shown in FIG. 2A-H, diuretic responses correlate with predictions from receptor binding studies. Analog peptides AP20, AP21, AP25, AP37, AP101, AP319 and AP324 of the invention significantly increased urine flow rate (urine volume) when infused at 5 μg/min, 5 μg/min, 5 μg/min, 10 μg/min, 5 μg/min, 10 μg/min and 10 μg/min respectively. Thus, these analog peptides, including R-S-S-C-F-G-G-R-I-D-R-I-G-A-C-N-S-F-R-Y,
R-S-S-C-F-G-G-R-I-D-R-I-G-C-N-S-F-R-Y,
R-S-S-C-R-I-D-R-I-G-A-Q-S-G-L-G-C-N-S-F-R-Y
C-F-G-G-R-I-D-R-I-G-A-C-NH$_2$,
A-F-G-G-R-I-G-A-NH$_2$,
[2-Naphthoxyacetyl]-G-G-R-I-R-I-NH$_2$ and

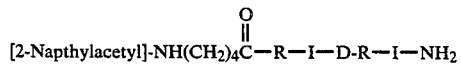

all cause significant diuresis in the rat.

On the other hand, AP54, which falls outside the scope of the compounds of the invention, and which was shown in Table IA to lack significant receptor binding activity, also appears inactive in vivo. These data, therefore, demonstrate the appropriate correlation between receptor binding activity and in vivo activity.

2. Diuresis and natriuresis in anesthetized dogs

The biological activity of analog compounds of the present invention can also be demonstrated in pentobarbital anesthetized dogs. In these examples, cannulae were placed in the left and right ureters and femoral vein of anesthetized dogs and urine was collected from the ureters. Analog peptides were administered via the femoral vein. Prior to infusing analog peptides, saline was infused for 30 minutes and urine was then collected for three ten minute collection periods. Urine volume was determined gravimetrically and urine sodium was determined photometrically.

Following these three baseline collection periods, the selected analog peptides were infused for 60 minutes and urinary flow was measure for an additional 60 minutes following infusion. During infusion (60 minutes) and recovery (60 minutes), ten minute collection periods were obtained. Control animals which received only saline were studied in parallel.

Data were examined by comparing urine flow rates for dogs infused with peptides AP101 (3 μg/kg/min), AP 306 (3 μg/kg/min), AP324 (3 μg/kg/min), or AP314 (1 μg/kg/min) against control animals infused with saline.

TABLE II

| Peptide | Dose (μg/kg/min) | Peak Urine Flow Rate V (ml/min) | Peak Urine Sodium Excretion $U_{Na}$ V (μEq/min) |
|---|---|---|---|
| Control | — | 0.61 | 40 |
| AP101 | 3 | 1.77* | |
| AP306 | 3 | 2.09* | |
| AP314 | 1 | 2.05* | 365* |
| AP324 | 3 | 2.47* | 495* |

As shown in Table II, the peak in vivo responses to the peptides are substantially above baseline (*$P<0.05$ by Student's test) and are interpreted as being statistically significant increases, comparable to the effects of native ANP compounds.

As noted previously, diuretic and natriuretic responses to peptides AP101, AP306, AP314 and AP324 correlate with predictions from receptor binding assays. Analog peptides AP101, AP306, AP314 and AP324, each of which are small linear peptides with substantial Ki(app)s, significantly increased urine flow rate (urine volume) and urinary sodium excretion when infused at 3, 3, 1 or 3 μg/kg/minute, respectively. Thus, these analog peptides are shown to each induce diuresis and natriuresis and therefore support the predictive value of the receptor binding analysis (Tables IA-D) for diuretic potency.

3. Blood pressure responses in anesthetized rats

Compounds of the present invention also lowered blood pressure when administered as a bolus or infusion to anesthetized rats. Table III presents data which compares the blood pressure effects of representative compounds of the present invention, including analog peptides AP20 and AP37, with that of rANP(126-150), following administraton by infusion.

TABLE III

| Peptide | Structure | Dose (p mol/kg/min) | Δ Blood Pressure |
|---|---|---|---|
| rANP(126-150) (126-150) | R—S—S—C—F—G—G— R—I—D—R—I—G—A—Q— S—G—L—G—C—N—S—F—R—Y | 183 | −39 ± 5 |
| AP20 | R—S—S—C—F—G—G— R—I—D—R—I—G—A— C—N—S—F—R—Y | 733 | −34 ± 3 |
| AP37 | C—F—G—G—R—I—D— R—I—G—A—C—NH$_2$ | 7330 | −14 ± 3 |

As shown, each of the analog peptides lowered blood pressure significantly. While analog peptide AP37 exhibited a weaker effect on blood pressure at a substantially higher dose (40x that of rANP(126-150)) it nevertheless was hypotensive. It has also been found tha analog peptides AP40, AP41 and AP57 exhibit activity similar to AP37.

Again, compounds which showed receptor binding affinity are shown to be active in vivo. The correlation between the in vitro receptor binding test and in vivo results further supports the validity of the receptor binding assay to show the therapeutic efficacy of the compounds tested.

Thus, the administration to mammalian hosts of therapeutically effective amounts of the additional disclosed analog peptides, or pharmaceutical compositions containing these analog peptides, can be used to substantially increase natriuresis and diuresis and/or alter the vascular caliber. Furthermore, administration of selected analog peptides within the scope of the present invention can be used to treat cases of hypertension or various edematous states whose etiology does not require the full range of biological activity provided by native ANP compounds.

C. Isolated Tissue Bioassays

It is believed, as stated above, that the effect of the analogs of the invention herein in vivo is due to their ability to potentiate the effect of endogenous ANP, possibly through blockage of the receptors involved in binding and clearing endogenous ANPs. Accordingly, one would expect that the diuretic and natriuretic effects of the analogs would be diminished or eliminated in isolated tissue where ANPs are not present unless specifically supplied. The results below demonstrate support for this theoretical model. As shown below, while a representative peptide of the invention, AP57, was active in vivo, it was not active in isolated perfused rat kidney. However, in the same model system, it was able to potentiate the effect of rANP(123-150).

1. Natriuresis and diuresis in the isolated perfused rat kidney

The biological actions of the ANP analogs can be demonstrated in the isolated perfused rat kidney, as described in Camargo, M. J. F. et al., Am. J. Physiol., 246: F447-F456 (1984). In a particular set of examples, the effect of the 15 amino acid peptide R-S-S-C-F-G-G-R-I-D-R-I-G-A-C-NH$_2$ (peptide AP57) at a concentration of $10^{-7}$M, was demonstrated in the intact kidney. The results were as presented in Table IV.

TABLE IV

EFFECT OF AP57 ON DOSE-RESPONSE CURVES OF rANP(123-150) IN THE ISOLATED PERFUSED RAT KIDNEY

| | GFR (ml/min) | FF (%) | RVR (mmHg/ml/min) | $U_{Na}V$ ($\mu$Eq/min) | $FE_{Na}$ V (%) $\mu$l/min |
|---|---|---|---|---|---|
| A. CONTROL KIDNEYS (N = 5) | | | | | |
| | 0.48 ± 0.06 | 121 ± 0.15 | 2.30 ± 0.12 | 0.37 ± 0.08 | 0.56 ± 0.09 16.5 ± 2.0 |
| B. AP57 ($10^{-7}$ M) (N = 4) | | | | | |
| | 0.55 ± 0.07 | 1.37 ± 0.22 | 2.27 ± 0.17 | 0.17 ± 0.04 | 0.24 ± 0.08 13.8 ± 2.0 |
| C. rANP (123-150) ($10^{-11}$ TO $10^{-8}$ M) (N = 4) | | | | | |
| [C] | | | | | |
| $10^{-11}$ | 0.45 ± 0.06 | 1.22 ± 0.20 | 2.29 ± 0.15 | 0.30 ± 0.05 | 0.50 ± 0.10 15.0 ± 1.8 |
| $10^{-10}$ | 0.53 ± 0.04 | 1.33 ± 0.20 | 2.36 ± 0.20 | 0.53 ± 0.14 | 0.72 ± 0.19 21.8 ± 1.7 |
| $10^{-9}$ | 0.66 ± 0.07 | 1.76 ± 0.29 | 2.51 ± 0.26 | 1.13 ± 0.43 | 1.21 ± 0.44 35.5 ± 5.7 |
| $10^{-8}$ | 0.82 ± 0.07 | 2.30 ± 0.41 | 2.64 ± 0.35 | 3.22 ± 0.92 | 2.78 ± 0.89 74.0 ± 14.8 |
| | 0.80 ± 0.08 | 2.23 ± 0.44 | 2.66 ± 0.32 | 4.78 ± 1.15 | 4.12 ± 0.94 96.6 ± 24.0 |
| D. rANP(123-150) ($10^{-11}$ to $10^{-8}$ M) IN PRESENCE OF AP57 ($10^{-7}$ M)[3] (N = 4) | | | | | |
| [C] | | | | | |
| $10^{-11}$ | 0.65 ± 0.06 | 1.57 ± 0.27 | 2.21 ± 0.21 | 0.17 ± 0.05 | 0.18 ± 0.04 16.3 ± 2.0 |
| $10^{-10}$ | 0.80 ± 0.08 | 2.04 ± 0.15 | 2.50 ± 0.15 | 0.45 ± 0.10 | 0.41 ± 0.11 31.0 ± 3.7 |
| $10^{-9}$ | 0.93 ± 0.04 | 2.65 ± 0.20 | 2.80 ± 0.31 | 1.76 ± 0.25 | 1.33 ± 0.20 70.6 ± 4.2 |
| $10^{-8}$ | 0.99 ± 0.07 | 2.81 ± 0.40 | 2.79 ± 0.34 | 6.03 ± 1.37 | 4.08 ± 0.72 139 ± 14 |
| | 0.84 ± 0.13 | 2.30 ± 0.47 | 2.63 ± 0.33 | 6.47 ± 2.29 | 4.77 ± 1.22 132 ± 33 |

GFR = glomerular filration rate;
FF = filtration fraction;
RVR = renal vascular resistance;
$U_{Na}V$ = uninary sodium excretion rate;
$FE_{Na}$ = fractional sodium excretion;
V = urine flow rate.

Results are presented as mean ± SE, with the number of kidneys presented for each test phase. In the phase demonstrating the effect of AP57 on the dose response curve of rANP (123-150), $10^{-7}$ M AP57 was added 30 minutes before the addition of increasing doses of rANP(123-150).

Despite having natriuretic and diuretic activities in an intact rat, analog peptide AP57 was not active in the isolated perfused rat kidney at a concentration of $10^{-7}$M (Table IV-Compare IV.B to IV.A).

Peptide AP57 was then tested for its ability to modulate the renal responses to the ANP S-L-R-R-S-S-C-F-G-G-R-I-D-R-I-G-A-Q-S-G-L-G-C-N-S-F-R-Y, designated rANP(123-150). As shown in Table IV, rANP(123-150) increases glomerular filtration rate, renal vascular resistance, filtration fraction, urinary sodium excretion rate, fractional excretion of sodium and urinary flow rate in a dose dependent manner in the concentration range from $10^{-11}$ to $10^{-7}$M. Also shown in Table IV, pretreatment of the isolated kidney with $10^{-7}$M AP57 causes the subsequent responses to rANP(123-150) to occur at reduced concentrations. Analog peptide AP57, despite being apparently inactive in this in vitro model, increased the potency of rANP(123-150). Thus, AP57 potentiates the activity of rANP(123-150). Subsequent assays have confirmed these observations and conclusions.

Table V shows that both rANP(123-150) and AP57 compete for specific [$^{125}$I]-rANP(123-150) binding to the cortex at the kidney.

TABLE V

| RATIO OF BOUND/FREE [$^{125}$I]-rANP(123-150) | | |
|---|---|---|
| | WHOLE KIDNEY | OUTER CORTEX |
| [$^{125}$I]-rANP (123-150) (4 × $10^{-12}$ M) (N = 3) | 122 ± 46 | 176 ± 23 |
| [$^{125}$I]-rANP (123-150) (4 × $10^{-12}$ M) + rANP(123-150) ($10^{-7}$ M) (N = 3) | 0.63 ± 0.27 | 0.77 ± 0.30 |
| [$^{125}$I]-rANP (123-150) (4 × $10^{-12}$ M) + | 1.27 ± 0.32 | 1.68 ± 0.44 |

TABLE V-continued

| RATIO OF BOUND/FREE [$^{125}$I]-rANP(123-150) | |
|---|---|
| WHOLE KIDNEY | OUTER CORTEX |

AP57
($10^{-7}$ M)
(N = 3)                                    5

These cortical-associated receptor sites may be involved in the clearance and removal of the ANPs. Thus, AP57 may block the clearance of rANP(123-150) in the isolated kidney model, thereby explaining its ability to potentiate the effects of rANP(123-150). Furthermore, if AP57 blocks clearance of endogenous ANPs, it may explain the natriuretic, diuretic and vasorelaxant responses to this peptides in vitro. Thus, AP57 and related analog peptides may modulate the activity of endogenous ANPs, possibly by altering clearance.

However, without necessarily defining the mechanism, the present application discloses a novel class of analog ANP peptide compounds of the general formula:

$$Z_1\text{-}AA_8\text{-}AA_9\text{-}AA_{10}\text{-}AA_{11}\text{-}AA_{12}\text{-}Z_2$$

wherein:
each of $AA_8$ and $AA_{11}$ is, independently, a basic/non-cyclic or neutral/non-polar/small or neutral/polar/non-cyclic amino acid residue:
each of $AA_9$ and $AA_{12}$ is, independently, a neutral/nonpolar/large/non-cyclic amino acid residue, including the D or L optical isomers thereof;
$AA_{10}$ is an acidic amino acid residue; and
$Z_1$ and $Z_2$ are as previously defined,
which have been shown to have natriuretic, diuretic, and/or hypotensive properties and thus, may have important therapeutic utility.

Although the foregoing invention has been described in some detail by way of clarity and for purposes of understanding, it will be understood by those skilled in the art that modifications of the invention may be practiced while remaining within the spirit and scope of the appended claims.

We claim:

1. A peptide having natriuretic, diuretic, and/or vasodilator activity in mammals which has the formula $$Y_1Y_2\text{-}R\text{-}I\text{-}D\text{-}R\text{-}I\text{-}Z_2$$

or $$Y_1\text{-}Y_2\text{-}R\text{-}M\text{-}D\text{-}R\text{-}I\text{-}Z_2,$$

wherein $Y_1$ is a hydrophobic group selected from the group consisting of phenyalanine, acetyl phenlalanine, desaminophenylalanine, fluorenyl, methyloxycarbonyl, benzyloxycarbonyl, diphenylpropionyl, triphenylpropionyl, 3-indolepropionyl, 4-indolebutyryl, 1-adamantylacetyl, 1-naphthylacetyl, 2-naphthylacetyl, 1-naphthyloxyacetyl, 2-naphthyloxyacetyl, CBZ, FMOC, 4-biphenylacetyl, and cyclohexylacetyl,
$Y_2$ is a spacer group which is a peptide of 1-2 amino acid residues selected from the group consisting of G, S, A, Aib, and Sar, or a residue of the formula —NH(CH$_2$)$_n$CO— wherein n is 3-6; and
$Z_2$ is NH$_2$ or NHR' wherein R' is a straight or branched chain alkyl of 1-6 carbons, or $Z_2$ is a peptide of 1-3 amino acid residues, said residues selected from the group consisting of G, A, S, Sar, and Aib or the amide or alkylamide form thereof.

2. A peptide selected from the group consisting of:
A-F-G-G-R-I-D-R-I-G-A-NH$_2$;

F-G-G-R-I-D-R-I-G-A-A-NH$_2$;

A-F-G-G-R-I-D-R-I-G-NH$_2$;

A-F-G-G-R-I-D-R-I-NH$_2$;

des NH$_2$-F-G-G-R-I-D-R-I-NH$_2$;

Y-A-F-G-G-R-I-D-R-I-G-A-NH$_2$;

F-G-G-R-I-G-R-I-G-A-NH$_2$;

F-G-G-R-I-D-R-I-NH$_2$

A-F-G-G-R-I-D-R-I-G-Y-NH$_2$;

A-F -G-G-R-I-D-R-I-G-A-NH$_2$;

A-F-A -G-R-I-D-R-I-G-A-NH$_2$;

A-F-G-A -R-I-D-R-I-G-A-NH$_2$;

(desNH$_2$-F)-G-G-R-I-D-R-I-G-A-NH$_2$;

(2-Naphthylacetyl)-G-G-R-I-D-R-I-G-A-NH$_2$;

(2-Naphthoxyacetyl)-NH(CH$_2$)$_4$CO-R-I-D-R-I-NH$_2$;

(1-Adamantylacetyl)-G-G-R-I-D-R-I-NH$_2$;

(FMOC)-G-G-R-I-D-R-I-NH$_2$;

(FMOC)-G-G-R-I-D-R-I-G-A-NH$_2$;

(Indolepropionyl)-G-G-R-I-D-R-I-G-A-NH$_2$;

(2-Naphthylacetyl)-G-G-R-I-D-R-I-NH$_2$;

(1-Naphthoxyacetyl)-G-G-R-I-D-R-I-NH$_2$;

(4-Biphenylacetyl)-G-G-R-I-D-R-I-NH$_2$;

(2-Naphthoxyacetyl)-G-G-R-I-D-R-I-G-A-NH$_2$;

(2-Naphthoxyacetyl)-G-G-R-I-D-R-I-NH$_2$;

(2-Naphthylacetyl)-G-Sar-R-I-D-R-I-NH$_2$ (2-Naphthylacetyl)-G-Aib-R-I-D-R-I-NH$_2$;

(2-Naphthoxyacetyl)-A -G-R-I-D-R-I-NH$_2$;

(FMOC)-NH(CH$_2$)$_4$CO-R-I-D-R-I-NH$_2$;

(2-Naphthylacetyl)-NH(CH$_2$)$_4$CO-R-I-D-R-I-NH$_2$;

(2-Naphthoxyacetyl)-NH(CH$_2$)$_5$CO-R-I-D-R-I-NH$_2$;

(2-Naphthylacetyl)-NH(CH$_2$)$_3$CO-R-I-D-R-I-NH$_2$ (2-Naphthylacetyl)-G-G-R-I-D-R-I-NHCH$_2$CH$_3$;

(2-Naphthylacetyl)-NH(CH$_2$)$_5$CO-R-I-D-R-I-NH$_2$;

(2-Naphthylacetyl)-S -G-R-I-D-R-I-NH$_2$;

(Diphenylpropionyl)-G-G-R-I-D-R-I-G-A-NH$_2$;
and (Cyclohexylacetyl)-G-G-R-I-D-R-I-NH$_2$ wherein the indicates that the residue to which it is attached is in the D configuration.

3. A protein which comprises the peptide of claim 1.

4. A composition useful as a natriuretic, diuretic and/or vasodilator comprising a therapeutically effective amount of the compound of claim 1 together with a pharmaceutically acceptable carrier.

5. A method for inducing natriuresis, diuresis, or vasodilation in a mammalian host, which comprises administering to said host a pharmaceutically effective amount of the composition of claim 4.

* * * * *

UNITED STATES PATENT AND TRADEMARK OFFICE
CERTIFICATE OF CORRECTION

PATENT NO. : 4,804,650
DATED : Feb. 14, 1989
INVENTOR(S) : John A. Lewicki, Robert M. Scarborough, Lorin K. Johnson It is certified that error appears in the above-identified patent and that said Letters Patent is hereby corrected as shown below:

At the top of column 51, Table V should read as follows:

|  | WHOLE KIDNEY | OUTER CORTEX |
|---|---|---|
| AP57 $(10^{-7}M)$ (N = 3) | 1.27 ± 0.32 | 1.68 ± 0.44 |

Signed and Sealed this

Eighteenth Day of July, 1989

Attest:

DONALD J. QUIGG

Attesting Officer

Commissioner of Patents and Trademarks